(12) United States Patent
Koch et al.

(10) Patent No.: US 9,724,135 B2
(45) Date of Patent: Aug. 8, 2017

(54) METHODS AND SYSTEMS FOR MINIMALLY INVASIVE POSTERIOR ARCH EXPANSION

(75) Inventors: David Koch, West Chester, PA (US); Simon Kamber, Oberdorf (CH); Reto Halbeisen, Dittingen (CH); Lukas Giger, Oberdorf (CH); Michael Guetlin, Oberdorf (CH); Felix Aschmann, Oberdorf (CH); Jann-Paul Suedkamp, Oberdorf (CH); Marco Messias, Oberdorf (CH); Tom Overes, Langendorf (CH); Bruno Laeng, Langendorf (CH); Roger Berger, Oberdorf (CH); Joern Richter, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 349 days.

(21) Appl. No.: 13/327,928

(22) Filed: Dec. 16, 2011

(65) Prior Publication Data
US 2012/0158061 A1   Jun. 21, 2012

Related U.S. Application Data

(60) Provisional application No. 61/424,127, filed on Dec. 17, 2010.

(51) Int. Cl.
*A61F 2/44* (2006.01)
*A61B 17/70* (2006.01)
(Continued)

(52) U.S. Cl.
CPC ...... *A61B 17/7071* (2013.01); *A61B 17/3421* (2013.01); *A61B 17/808* (2013.01);
(Continued)

(58) Field of Classification Search
CPC ............ A61B 17/7071; A61B 17/7074; A61B 17/7076; A61F 2002/30736; A61F 2002/2839; A61F 2/4405; A61F 2/46
(Continued)

(56) References Cited

U.S. PATENT DOCUMENTS 3,486,505 A    12/1969 Morrison
5,306,308 A *  4/1994 Gross et al. ............... 623/17.16
(Continued)

FOREIGN PATENT DOCUMENTS

JP       0H0638936 U *  5/1994 ......... A61B 17/7071
WO    WO 2009/101539      8/2009

OTHER PUBLICATIONS

JPH0638936 pdf translation, Nov. 2, 2016.*
(Continued)

*Primary Examiner* — Atiya Mahmud
(74) *Attorney, Agent, or Firm* — Baker & Hostetler LLP

(57) ABSTRACT

Provided are methods and systems for enlarging a spinal canal of a vertebra. Using the methods and systems disclosed the spinal canal of the vertebra is enlarged by cutting the posterior arch portion of the vertebra to create one or two implant receiving spaces in the posterior arch portion. The cutting of the posterior arch portion is completed through a minimally invasive approach. Once cut, the detached portion of the posterior arch portion is repositioned and an implant is positioned in the implant receiving space of the posterior arch portion to thereby enlarge the spinal canal such that the spinal cord is no longer compressed. The insertion of the implant is also completed through a minimally invasive approach.

36 Claims, 25 Drawing Sheets

(51) Int. Cl.
  *A61B 17/34* (2006.01)
  *A61B 17/80* (2006.01)
  *A61F 2/46* (2006.01)
  *A61B 17/16* (2006.01)
  *A61F 2/30* (2006.01)

(52) U.S. Cl.
  CPC .......... *A61F 2/4405* (2013.01); *A61F 2/4611* (2013.01); *A61B 17/1671* (2013.01); *A61B 17/3468* (2013.01); *A61F 2002/30736* (2013.01); *A61F 2002/30789* (2013.01); *A61F 2002/30843* (2013.01); *A61F 2002/4628* (2013.01)

(58) Field of Classification Search
  USPC .................... 606/86 A, 99; 623/17.11, 17.16
  See application file for complete search history.

(56) References Cited

U.S. PATENT DOCUMENTS

| | | | |
|---|---|---|---|
| 6,200,322 B1* | 3/2001 | Branch et al. | 606/96 |
| 6,743,256 B2* | 6/2004 | Mason | 623/17.16 |
| 8,262,731 B2* | 9/2012 | Songer et al. | 623/17.14 |
| 8,491,658 B1* | 7/2013 | Etminan | 623/17.16 |
| 8,721,722 B2* | 5/2014 | Shah et al. | 623/17.15 |
| 2001/0020186 A1* | 9/2001 | Boyce et al. | 623/17.16 |
| 2003/0004517 A1 | 1/2003 | Anderson | |
| 2004/0143332 A1* | 7/2004 | Krueger et al. | 623/17.14 |
| 2005/0021042 A1* | 1/2005 | Marnay et al. | 606/99 |
| 2005/0075643 A1* | 4/2005 | Schwab et al. | 606/90 |
| 2005/0107877 A1* | 5/2005 | Blain | 623/16.11 |
| 2005/0149035 A1* | 7/2005 | Pimenta et al. | 606/86 |
| 2005/0165487 A1* | 7/2005 | Muhanna et al. | 623/17.15 |
| 2005/0261772 A1* | 11/2005 | Filippi et al. | 623/17.13 |
| 2005/0273100 A1 | 12/2005 | Taylor | |
| 2006/0030861 A1* | 2/2006 | Simonson et al. | 606/99 |
| 2006/0195097 A1* | 8/2006 | Evans et al. | 606/61 |
| 2006/0241641 A1* | 10/2006 | Albans et al. | 606/90 |
| 2007/0255415 A1* | 11/2007 | Edie et al. | 623/17.16 |
| 2007/0270866 A1* | 11/2007 | von Jako | 606/86 |
| 2009/0048604 A1 | 2/2009 | Milz et al. | |
| 2009/0054991 A1* | 2/2009 | Biyani et al. | 623/17.16 |
| 2009/0292361 A1* | 11/2009 | Lopez | 623/17.15 |
| 2010/0057127 A1 | 3/2010 | McGuire et al. | |
| 2010/0114100 A1 | 5/2010 | Mehdizade | |
| 2010/0114183 A1 | 5/2010 | Wassinger et al. | |
| 2010/0152854 A1 | 6/2010 | Slivka et al. | |

OTHER PUBLICATIONS

International Patent Application No. PCT/US2011/065325: International Search Report and Written Opinion dated May 4, 2012, 23 pages.

Synthes® Technique Guide: "ARCH Laminoplasty System. Dedicated System for Open-door Laminoplasty," Synthes GmbH, © Apr. 2010, 1-20.

* cited by examiner

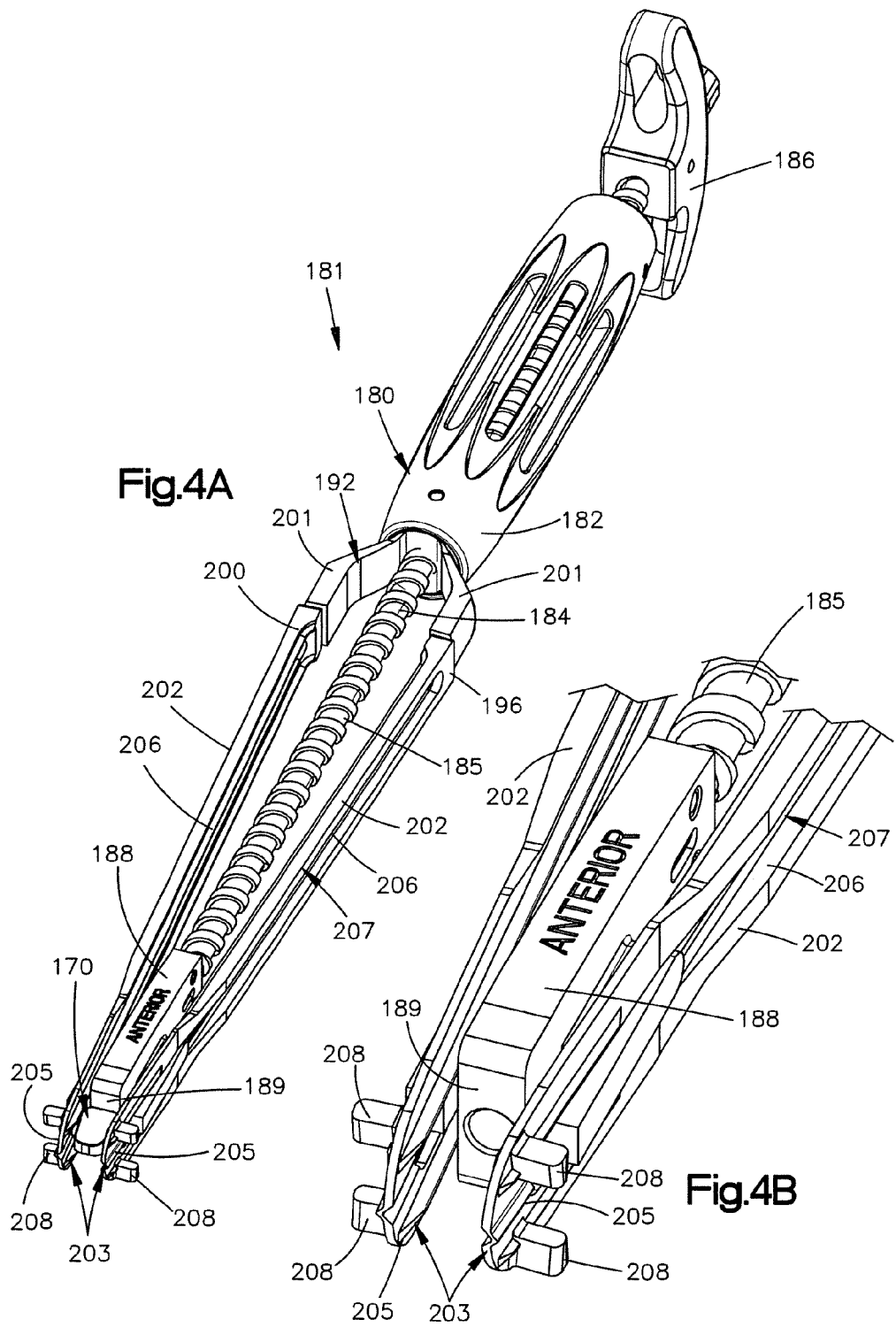

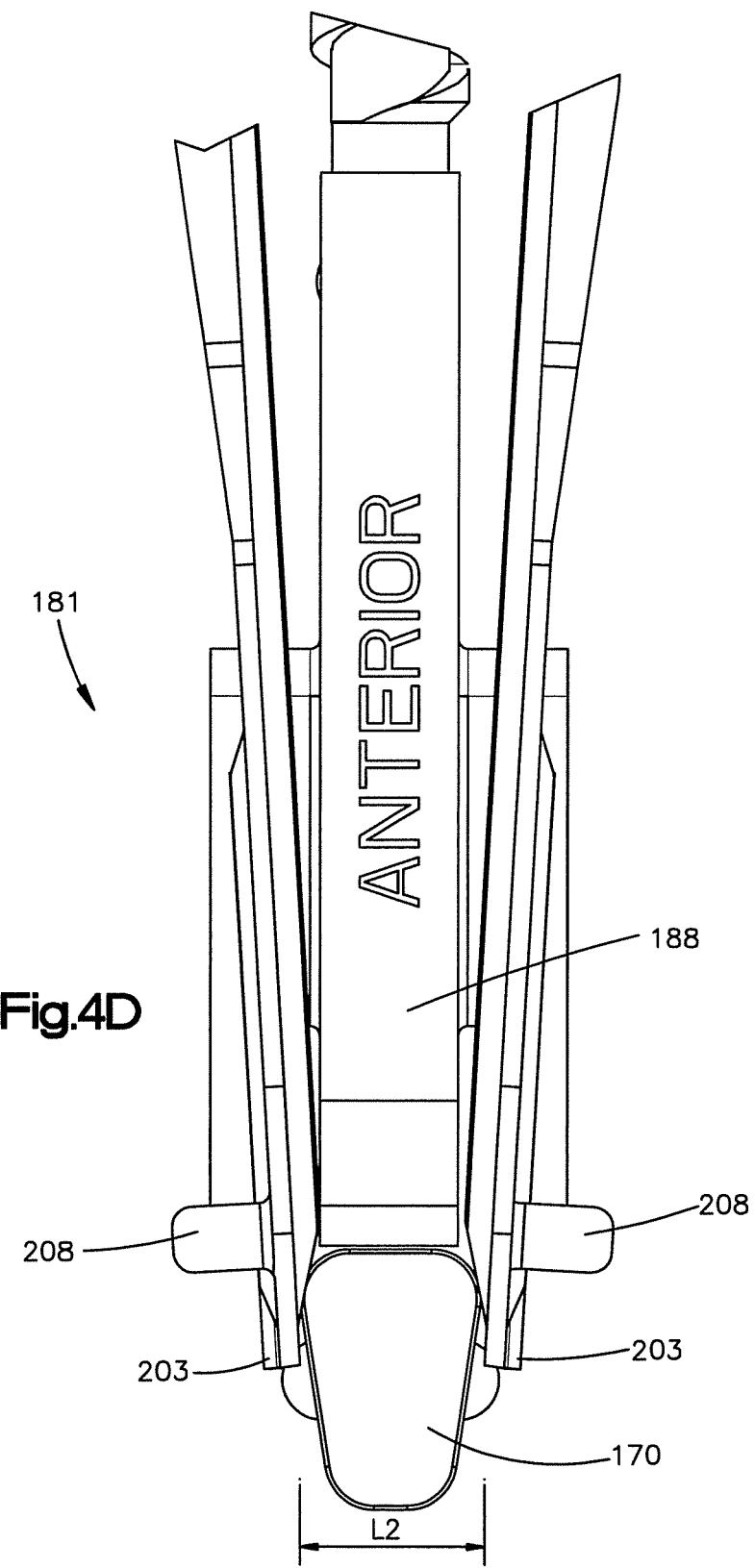

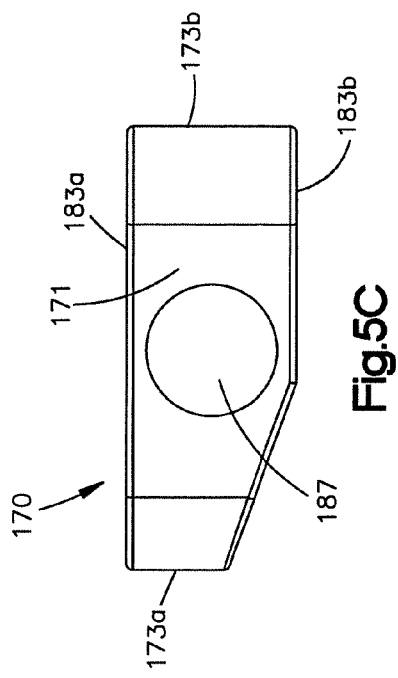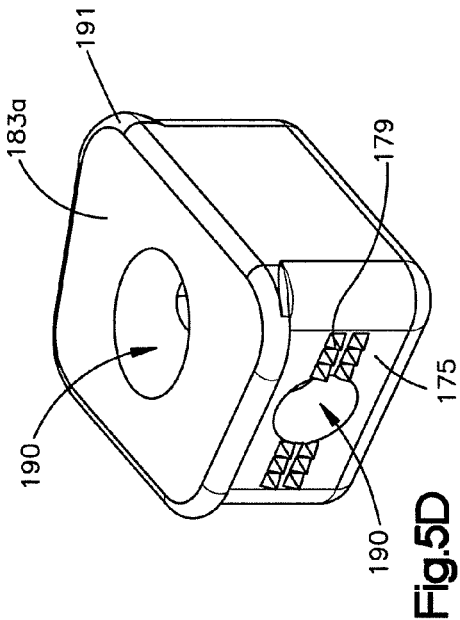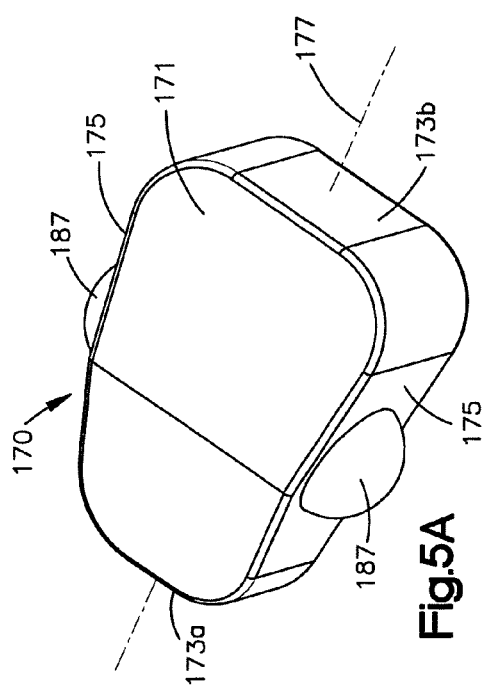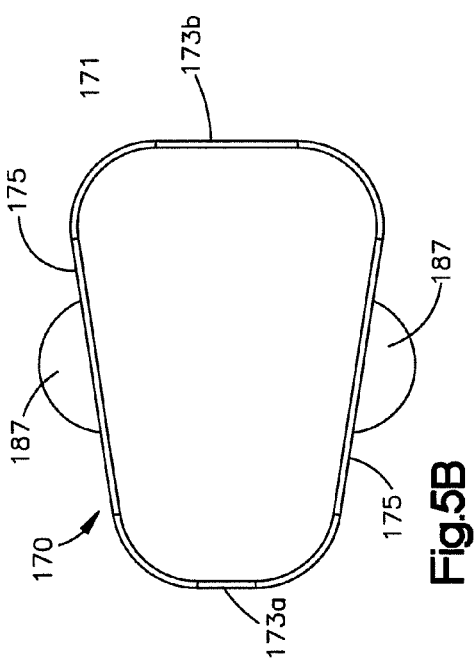

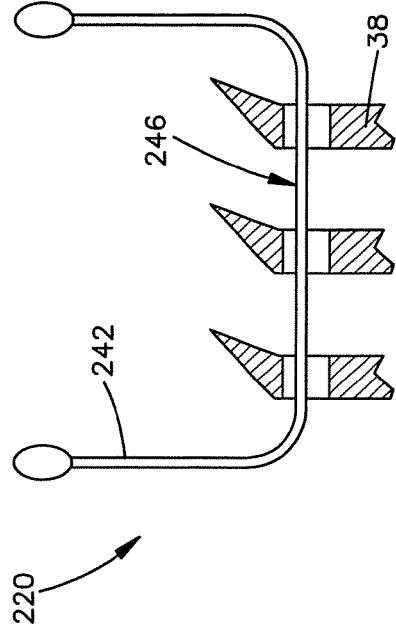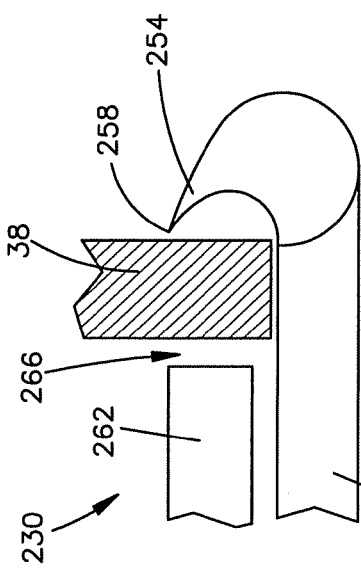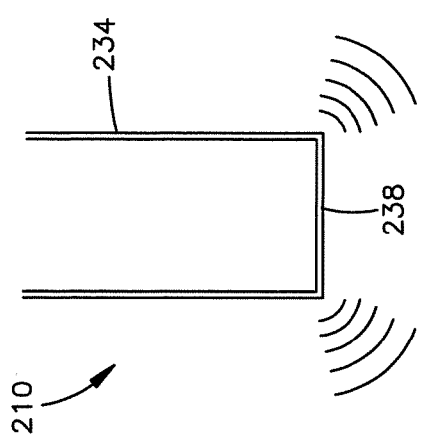

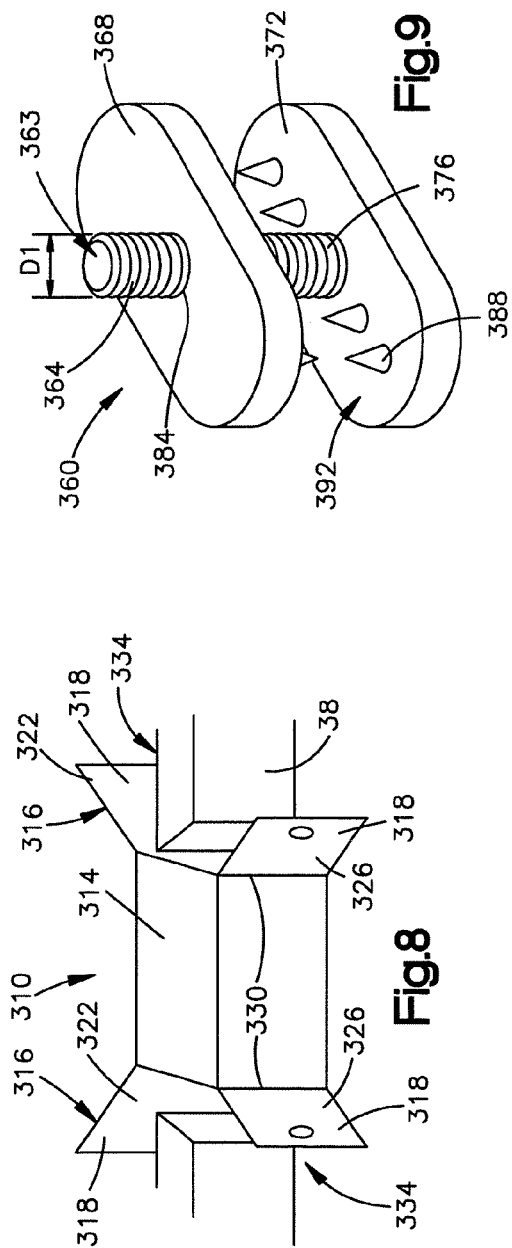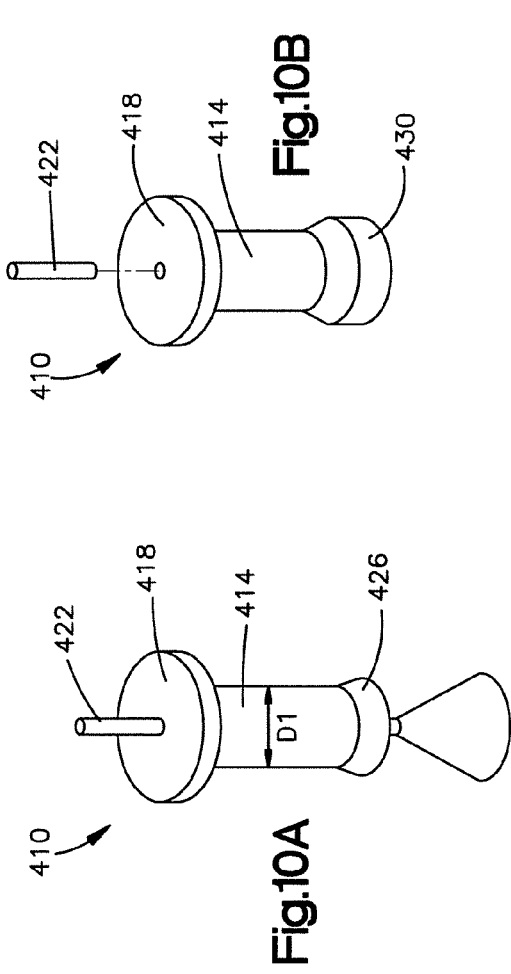

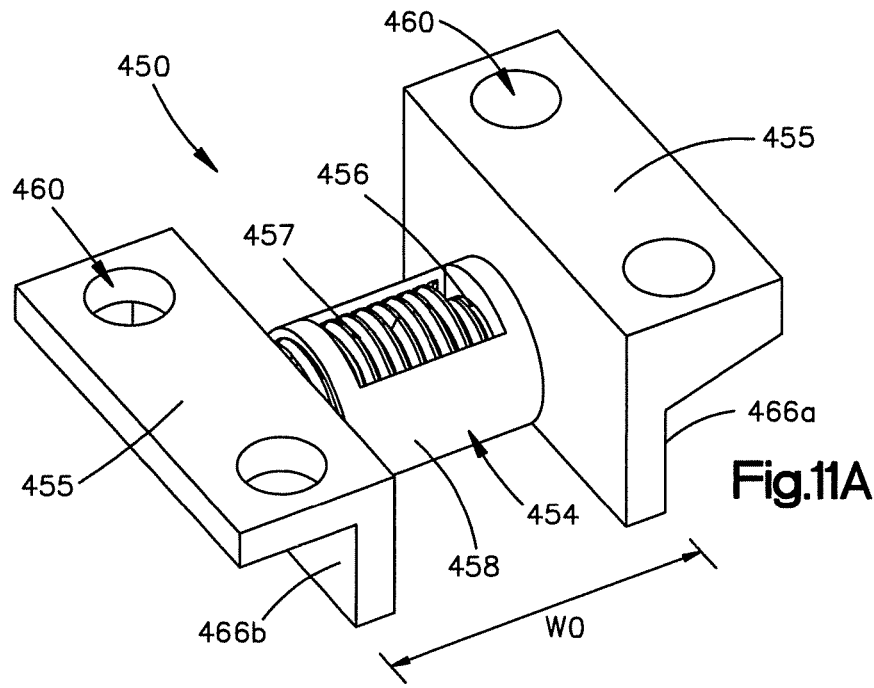
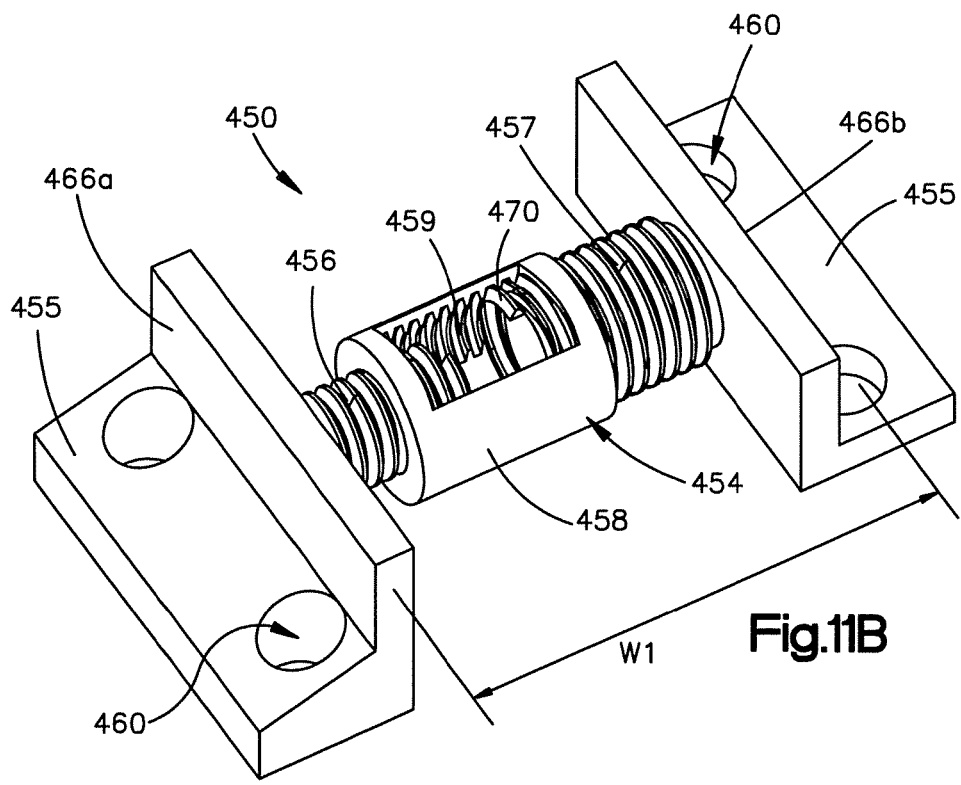

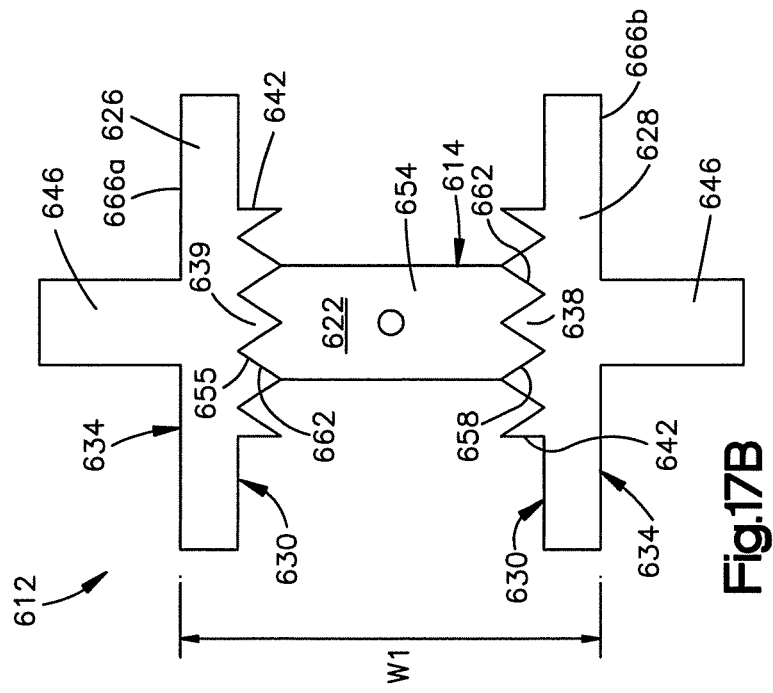
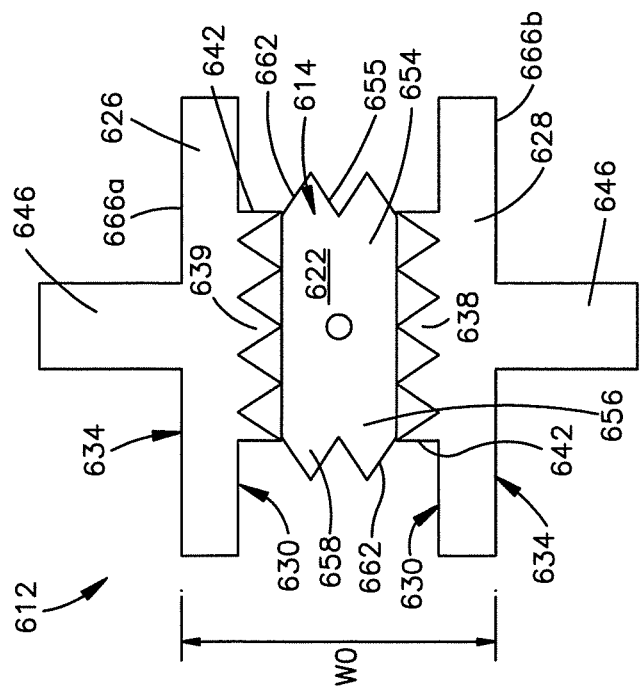

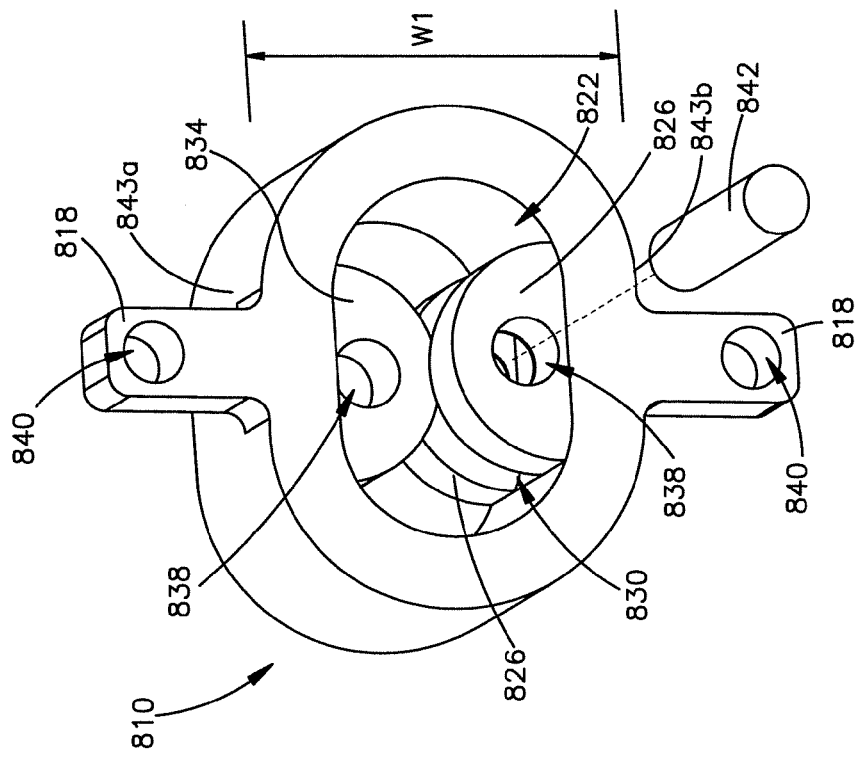
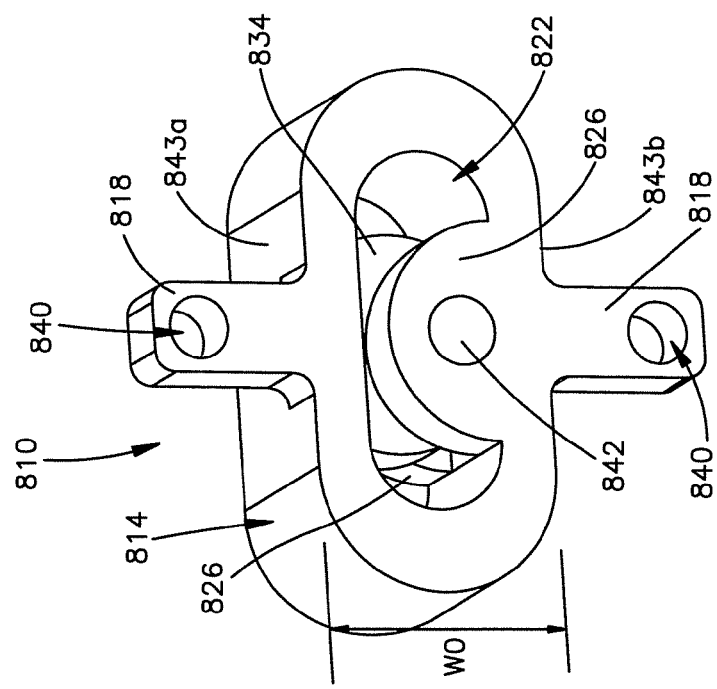

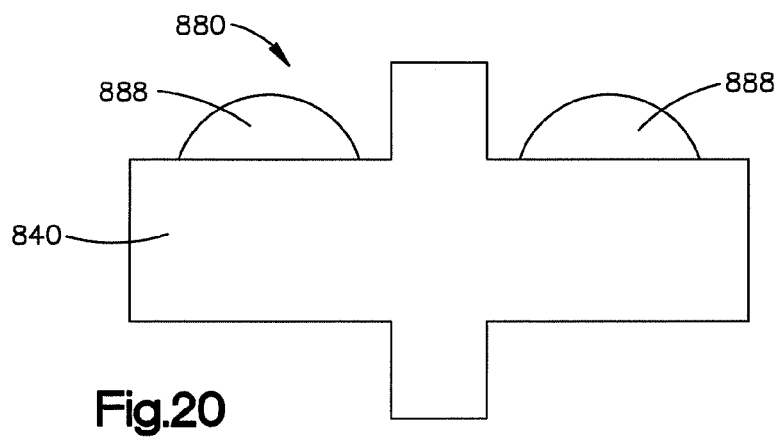
Fig.20
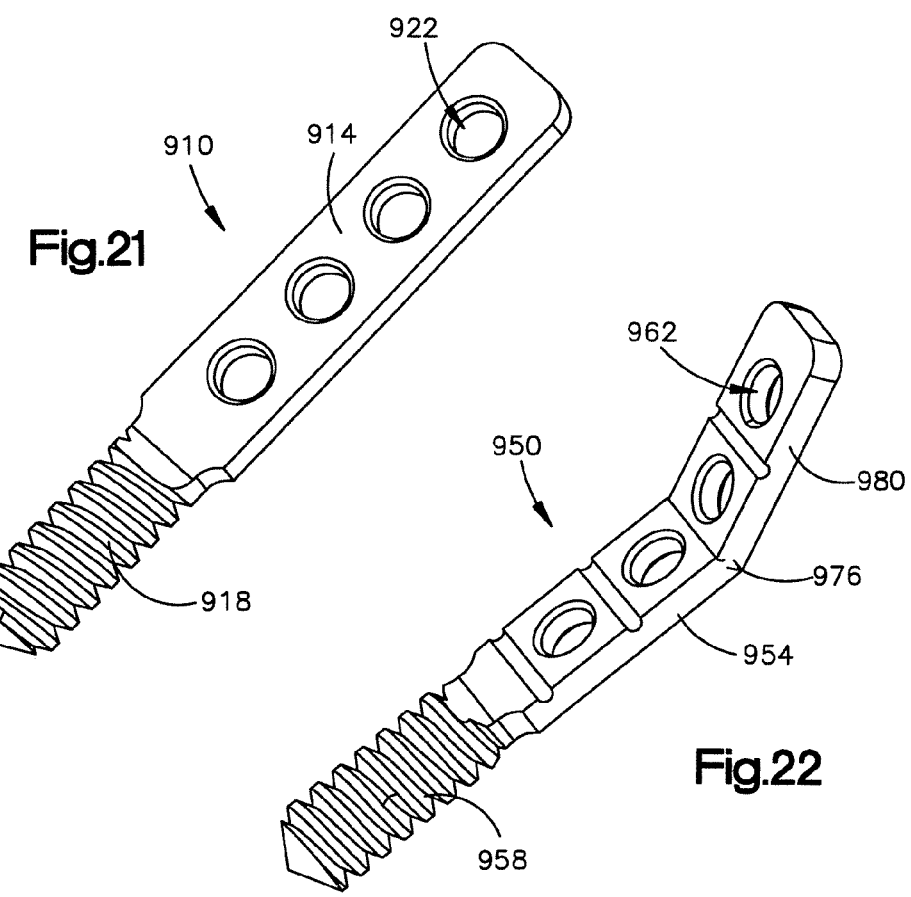
Fig.21
Fig.22

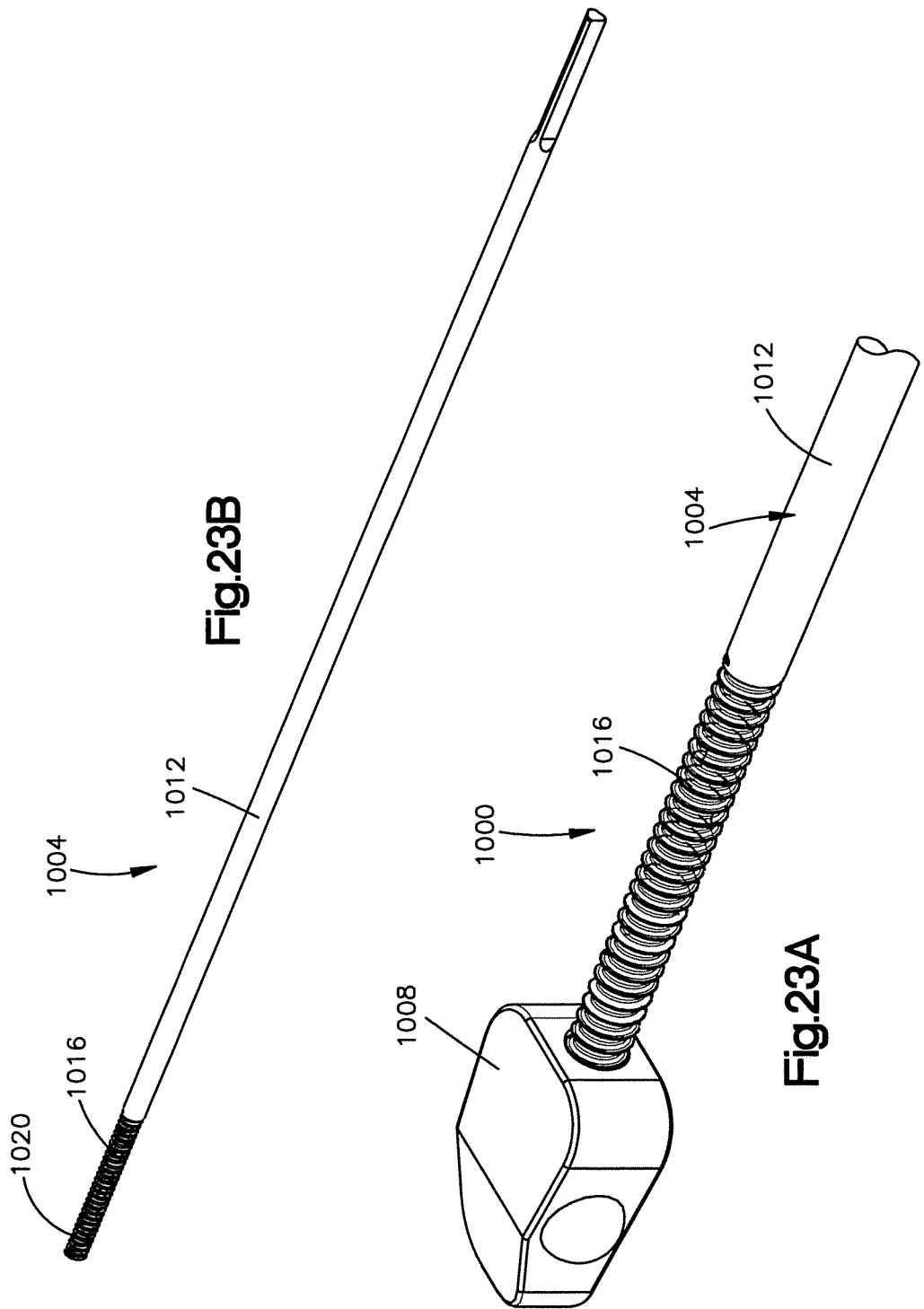

METHODS AND SYSTEMS FOR MINIMALLY INVASIVE POSTERIOR ARCH EXPANSION

CROSS REFERENCE TO RELATED APPLICATIONS

This application claims the benefit of U.S. Provisional Application Ser. No. 61/424,127 filed Dec. 17, 2010 the disclosure of which is hereby incorporated by reference in its entirety herein.

BACKGROUND

The spine is susceptible to various medical conditions that reduce the area within the vertebra available for the spinal cord and nerve roots. For instance, spinal stenosis is a condition in which the spinal canal narrows and compresses the spinal cord and nerve roots. Spinal stenosis may be caused by many medical conditions, such as the calcification and thickening of the ligaments of the spine (e.g., from deposits of calcium salts), enlargement of bones and joints, formation of osteophytes (bone spurs), a herniated (bulging)) disk, and diseased bone or tumors may result in an ingrowth into the spinal cord area. Thus, the amount of anatomical space available for the spinal cord and nerve roots that emanate from the spinal cord can be reduced, which often results in lower back pain as well as pain or abnormal sensations in the extremities. Spinal stenosis may affect the cervical, thoracic or lumbar spine.

Surgical procedures are available for treating spinal stenosis by relieving pressure on the spinal cord through posterior arch expansion. The conventional surgical procedures typically involve first making an incision in the back and stripping muscles and supporting structures away from the spine to expose the posterior portion of the vertebral column. Once exposed, the spinal canal may be widened (i.e. the posterior arch may be expanded), either by removing the lamina (laminectomy) or by cutting the lamina and then spreading it apart with an implant (laminoplasty). The invasive nature of conventional posterior arch expansion methods often result in significant post-operative pain and long patient recovery times.

SUMMARY

In accordance with an embodiment, a minimally invasive posterior arch expansion system is configured to expand a spinal canal. The system can include an access assembly that is configured to form a minimally invasive access path to an implant receiving space defined by first and second opposed posterior arch surfaces. The system can further include a spreading device and an implant. The spreading device is configured to extend through the minimally invasive access path of the access assembly and engage the implant receiving space to thereby widen the implant receiving space such that the first and second posterior arch surfaces move away from each other. The implant is configured to be implanted in the implant receiving space. The system further includes an inserter tool that is configured couple to the implant and is configured to extend through the minimally invasive access path of the access assembly to thereby insert the implant into the implant receiving space.

BRIEF DESCRIPTION OF THE DRAWINGS

The foregoing summary, as well as the following detailed description of a preferred embodiment of the application, will be better understood when read in conjunction with the appended drawings. For the purposes of illustrating the minimally invasive procedure and systems of the present application, there is shown in the drawings several embodiments. It should be understood, however, that the application is not limited to the precise arrangements and instrumentalities shown. In the drawings:

FIG. 4A is a perspective view of an implant assembly constructed in accordance with an embodiment, the implant assembly including an implant inserter tool and an implant coupled to the implant inserter tool, the implant inserter tool configured to expand the implant receiving space as the implant is inserted into the implant receiving space;

FIG. 4B is an expanded perspective view of a distal portion of the implant inserter tool shown in FIG. 4A, the implant inserter tool having a spreading device that includes distal engagement portions that are configured to engage the implant receiving space;

FIG. 4D is an expanded front elevation view of the distal portion of the implant inserter tool shown in FIG. 4C, the engagement portions of the spreading device having a second position whereby the engagement portions are separated by a second distance that is greater than the first distance to thereby widen the implant receiving space so that the implant can be implanted into the implant receiving space;

FIG. 5A is a perspective view of the implant shown in FIG. 4A;

FIG. 5B is a top plan view of the implant shown in FIG. 5A;

FIG. 5C is a side elevation view of the implant shown in FIG. 5A;

FIG. 5D is a perspective view of an implant in accordance with another embodiment, the implant including a lip and a plurality of teeth that are configured to engage the lamina;

FIG. 7A is a schematic view of a cutting tool system constructed in accordance with another embodiment, the cutting tool system including a cutting tool that produces ultrasonic waves configured to cut into the posterior arch portion;

FIG. 7B is a schematic view of a cutting tool system constructed in accordance with another embodiment, the cutting tool system including a cutting tool defined as an abrasive wire that is configured to cut into the posterior arch portion;

FIG. 7C is a schematic view of a cutting tool system constructed in accordance with another embodiment, the cutting assembly including a cutting tool defined as a rib cutter that is configured to cut into the posterior arch portion;

FIG. 8 is a side perspective view of an implant constructed in accordance with another embodiment, the implant including a body and a pair of engagement members that extend from the body, each engagement member defining two wings that are configured to be coupled to the posterior arch portion;

FIG. 9 is a side perspective view of an implant constructed in accordance with another embodiment, the implant including a threaded body and a pair of engagement members, at least one of the engagement members is configured to move along the threaded body to thereby affix the implant to the posterior arch portion;

FIG. 10A is a side perspective view of an implant constructed in accordance with another embodiment, the implant including a body, a first engagement member, and a mandrel extending through the body;

FIG. 10B is a side perspective view of the implant shown in FIG. 10A after the mandrel has been translated proximally to thereby form a second engagement member;

FIG. 11A is a perspective view of an implant constructed in accordance with another embodiment, the implant including an expandable body having first and second threaded portions coupled together with an expansion mechanism such that rotation of the expansion mechanism causes the implant to expand;

FIG. 11B is a perspective view of the implant shown in FIG. 11A in an expanded configuration or position;

FIG. 17A is a side elevation view of an implant constructed in accordance with another embodiment, the implant including engagement members configured as keels capable of engaging the keel cuts defined by the implant receiving space of the posterior arch portion shown in FIG. 16, the implant further including a rotatable member that is configured expand the implant upon rotation of the rotatable member by 90 degrees;

FIG. 17B is a side elevation view of the implant shown in FIG. 17A in an expanded configuration or position;

FIG. 19A is a perspective view of an implant constructed in accordance with another embodiment, the implant including an expandable body that defines a deformable O-ring that is locked in a compressed position with a locking pin;

FIG. 19B is a perspective view of the implant shown in FIG. 19A in an expanded position after the pin has been removed;

FIG. 20 is a side elevation view showing an implant constructed in accordance with another embodiment, the implant having stops that are configured to prevent the implant from being over inserted into the implant receiving space of the posterior arch portion shown in FIG. 16;

FIG. 21 is a perspective view of an implant constructed in accordance with another embodiment, the implant having a flat paddle member and a screw that extends from the paddle member, the screw is configured to engage the posterior arch portion, and the paddle member is configured to be attached to the lamina with a fastener;

FIG. 22 is a perspective view of an implant constructed in accordance with another embodiment, the implant including a paddle member having a hinged portion;

FIG. 23A is a perspective view of an implant assembly constructed in accordance with another embodiment, the implant assembly including an inserter tool configured as a threaded rod, and an implant configured to be engaged by the threaded rod to thereby couple the implant to the threaded rod; and FIG. 23B is a perspective view of the inserter tool shown in FIG. 23A.

DETAILED DESCRIPTION

Figure 1B:
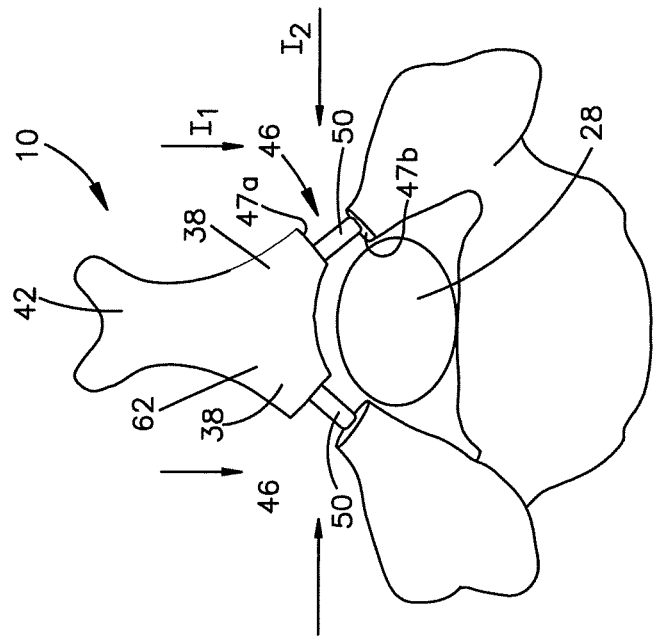
FIG. 1B is a top plan view of the vertebra shown in FIG. 1A expanded in accordance with an embodiment, the vertebra having first and second implant receiving spaces formed in the first and second portions of the lamina and first and second implants implanted into the first and second implant receiving spaces to thereby expand the spinal canal.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the system and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

The spine is comprised of a series of vertebra that are stacked on top of each other from the bottom of the skull to the pelvis. Each vertebra is composed of several parts that act as a whole to surround and protect the spinal cord and nerves. In particular and in reference to FIG. 1A, each vertebra 10 includes a spinal canal 14 that is defined by an anterior portion 18, opposed lateral portions 22, and a posterior arch portion 26. The spinal canal 14 protects a spinal cord 28 that passes through the spinal canal 14 of each vertebra 10. As shown, the anterior portion 18 is composed of a vertebral body 30 that is the main portion of the vertebra 10. The opposed lateral portions 22 of the vertebra 10 are pedicles 34 which are cylinder-shaped projections that extend out from the posterior side of the vertebral body 30. The posterior arch portion 26 is composed of a lamina 38 and a spinous process 42 that extends out from a midline of the lamina 38. The lamina 38 acts as a roof of the spinal canal 14 and provides support and protection for the posterior side of the spinal cord 28.

Figure 1A:
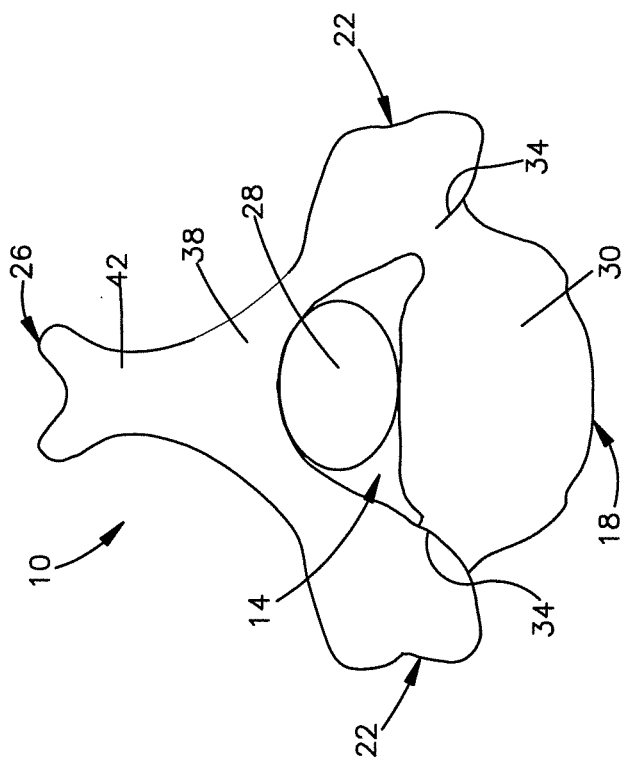
FIG. 1A is a top plan view of a vertebra having a narrowed spinal canal, the vertebra including a posterior arch portion having a lamina and a spinous process separating the lamina into first and second portions.
Figure 1D:
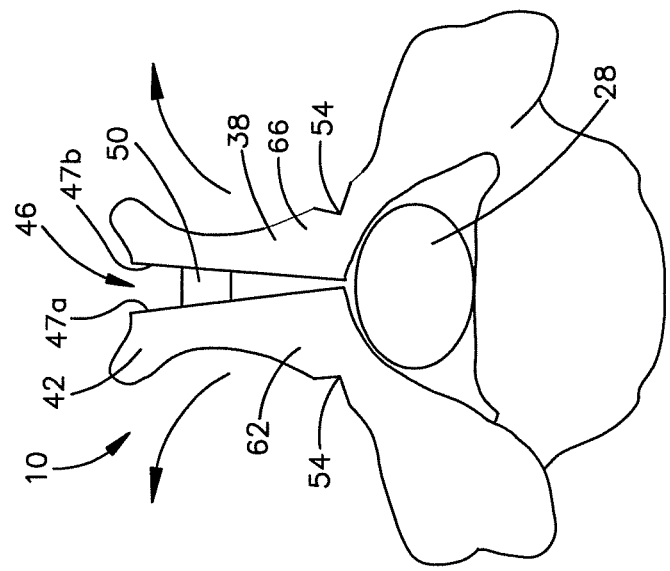
FIG. 1D is a top plan view of the vertebra shown in FIG. 1A expanded in accordance with another embodiment, the vertebra having first and second hinges formed in the first and second portions of the lamina, an implant receiving space formed in the spinous process, and an implant implanted into the implant receiving space to thereby expand the spinal canal.
Figure 1C:
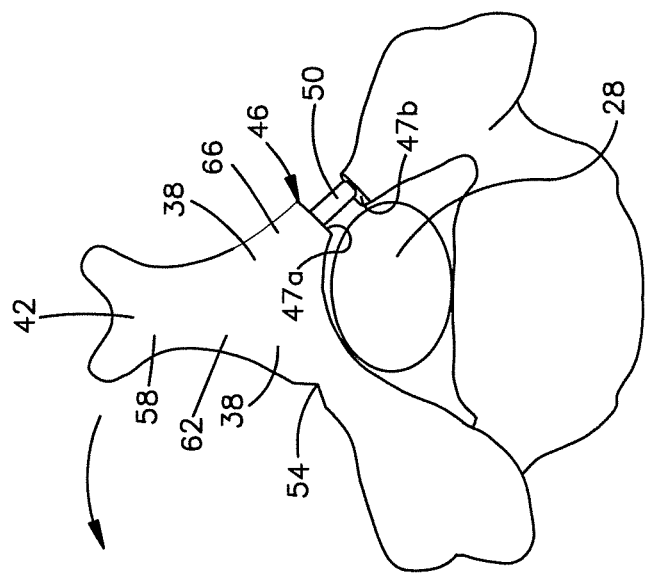
FIG. 1C is a top plan view of the vertebra shown in FIG. 1A expanded in accordance with another embodiment, the vertebra having a hinge formed in the first portion of the lamina, and implant receiving space formed in the second portion of the lamina, and an implant implanted into the implant receiving space to thereby expand the spinal canal.

In reference to FIG. 1A, the spinal canal 14 of the vertebra 10 shown, has narrowed and the spinal cord 28 that runs through the spinal canal 14 is impinged upon by the surrounding boney parts that define the spinal canal 14. As a result, extreme discomfort may be experienced by the patient. The spinal canal 14 can thus be widened through posterior arch expansion, as shown in FIGS. 1B, 1C, and 1D, to remove the impingement on the spinal cord 28. The posterior arch expansion can include for example cutting through the lamina (i.e. laminoplasty) or cutting through the spinous process.

To widen the spinal canal 14, the lamina 38 can be cut on one or both sides of the spinous process 42 to form one or two corresponding implant receiving spaces 46 (e.g., at least one implant receiving space 46) in the lamina 38, as shown in FIG. 1B. That is once cut, the lamina 38 can define opposed first and second posterior arch surfaces 47a and 47b, and the implant receiving space 46 can be defined between the first and second posterior arch surfaces 47a and 47b. The spinal canal 14 may be enlarged by inserting an implant 50 into each implant receiving space 46 of the lamina 38. As shown in FIG. 1B, once the implants 50 are fully inserted into the implant receiving spaces 46, the spinal canal 14 is expanded and the spinal cord 28 is no longer pinched. The lamina 38 can be approached, for instance, in a posterior approach $I_1$ or a medial-lateral approach $I_2$.

Alternatively, the spinal canal 14 may be widened by cutting the lamina 38 to form a single implant receiving space 46 as shown in FIGS. 1C and 1D. For instance, the lamina 38 can be cut only a portion of the way such as half way through a first portion 62 of the lamina 38 on one side of the spinous process 42 to form a hinge 54, and all of the way through a second portion 66 of the lamina 38 on the other side of the spinous process 42 to form the implant receiving space 46. A first portion 62 of the lamina 38 is then rotated about the hinge 54 and the implant 50 is inserted into the implant receiving space 46 to thereby widen the spinal canal 14. As will be appreciated from the description herein, the posterior arch expansion system can be configured to cut partially into or through the lamina 38 at one or both sides with respect to the spinous process 42.

The spinal canal 14 may also be widened with a single implant receiving space 46 by cutting through the middle of the spinous process 42 as shown in FIG. 1D, such that the spinous process 42 defines the implant receiving space 46. For instance hinges 54 can be formed on both sides of the spinous process 42 in the first and second portions 62 and 66 of the lamina 38. The first and second portions 62 and 66 of the lamina 38 that are disposed between the spinous process 42 and the hinges 54 can then be rotated about their respective hinges 54, so as to widen the implant receiving space 46 and correspondingly widen the spinal canal 14. The implant 50 can then be inserted into the implant receiving space 46 to fix the spinal canal 14 in its widened configuration. It should be appreciated, however, the first and second portions 62 and 66 of the lamina may be weak enough that hinges 54 do not have to be formed.

For each of the above identified procedures, the lamina 38 can be accessed, cut, and widened using a minimally invasive approach so as to limit damage to the patient's surrounding tissue and muscle, thereby further limiting patient recovery time. The minimally invasive approach can be performed using a minimally invasive posterior arch expansion system that includes at least one of an access assembly such as access assembly 59 shown in FIGS. 2A-2B, a cutting tool system, such as cutting tool system 98 shown in FIGS. 3A-3B, and an implant assembly, such as implant assembly 181 shown in FIGS. 4A-4D. The posterior arch expansion system or one or more of its components can be included in a kit that includes multiple implants and instruments.

Figure 2A:
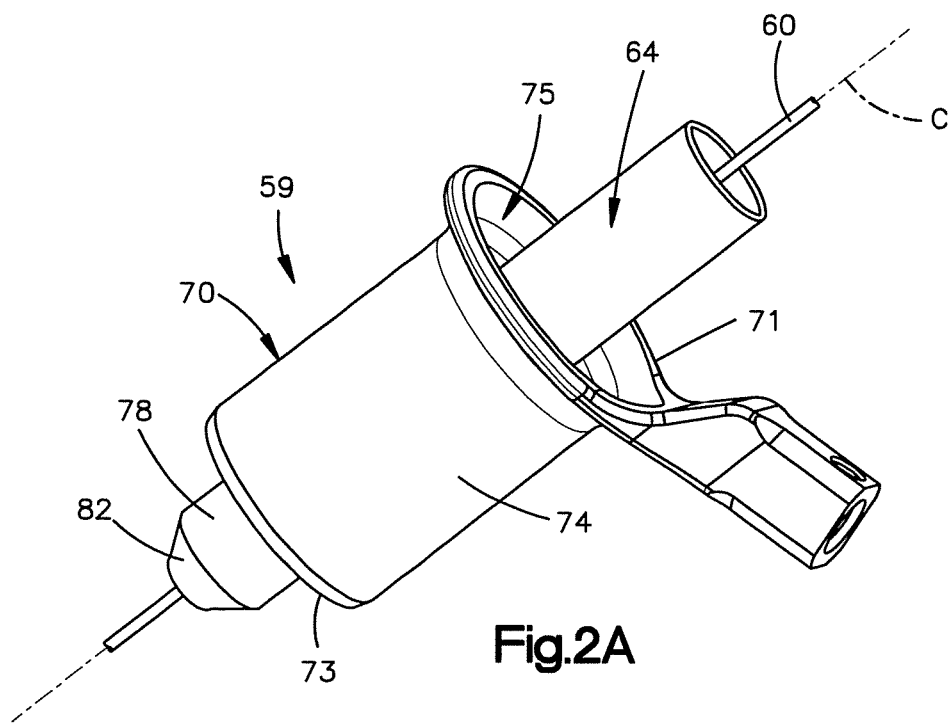
FIG. 2A is a perspective view of an access assembly including a K-wire, a dilator disposed over the k-wire, and a cannula disposed over the dilator, the cannula defining a passageway that forms a minimally invasive access path to the posterior arch portion such as to the lamina.
Figure 2B:
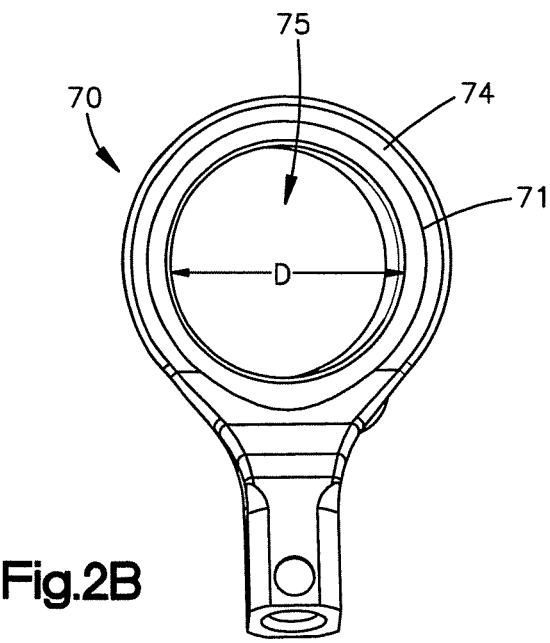
FIG. 2B is a top plan view of the cannula shown in FIG. 2A.

Referring to FIGS. 2A-2B, the access assembly 59 is configured to penetrate the tissue to create or otherwise form a minimally invasive access path to the first portion 62 of the lamina 38. For instance and as shown in FIG. 2A, the access assembly 59 includes a K-wire 60 that can be inserted at a location proximate to the lamina 38. The access assembly 59 can further include one or more dilators 64 that can be passed over the wire 60 to thereby incrementally widen the access path to the lamina 38 until the access path is sized as desired. As shown in FIGS. 2A and 2B, the access assembly 59 can further include an access member, illustrated as a cannula 70 that is slid over the outer dilator 64 toward the first portion 62 of the lamina 38 once the access path has reached the desired size. As shown, the cannula 70 includes an elongate body 74 that is elongate along a longitudinal axis C. The cannula 70 further includes a passageway 75 that extends through the body 74 along the longitudinal axis C and defines a cross-section, such as a diameter D. The body 74 defines a first proximal end 71 that is configured to be external from the patient's body once the cannula 70 has been fully inserted into the access path, and an opposed distal end 73 that is spaced from the proximal end 71 along the longitudinal axis C, and is configured to be disposed proximate to the proximal portion of the vertebra, for example at the lamina 38. In embodiments where a vertebra of the cervical spine is being operated on, the cannula 70 can have a diameter between about 10 mm and about 25 mm, and in embodiments where a vertebra of the lumbar spine is being operated on, the cannula 70 can have a diameter between about 15 mm and about 50 mm. In this way, the cannula 70 provides a minimally invasive access path for the procedure. It should be appreciated, however, that the minimally invasive access path can have other cross sectional dimensions so long as minimal trauma is caused to the surrounding muscle of the vertebra being operated on. Moreover, it should be appreciated that the access assembly 59 can be configured to penetrate the tissue to create or otherwise form a minimally invasive access path to other portions of the posterior arch portion 26 such as to the spinous process 42.

As shown in FIG. 2A, the dilators 64 may include a cylindrical body 78 having a tapered distal end 82. The tapered end 82 allows the tissue to expand as the dilators 64 are inserted. It should be appreciated, however, that the dilators 64 may include other configurations. For example, the dilators 64 can include oblong body so long as the dilators incrementally increase in diameter, and are configured to be slid over each other until the desired workspace or access path cross sectional dimension is achieved.

It should be appreciated that other methods and procedures may be performed using the posterior arch expansion system or components thereof so as to create the minimally invasive access path to the vertebra. For example, the tissue can be cut toward the vertebra using a scalpel or any suitable alternative access member such as a retractor can be inserted through the soft tissue to access the vertebra.

Figure 3A:
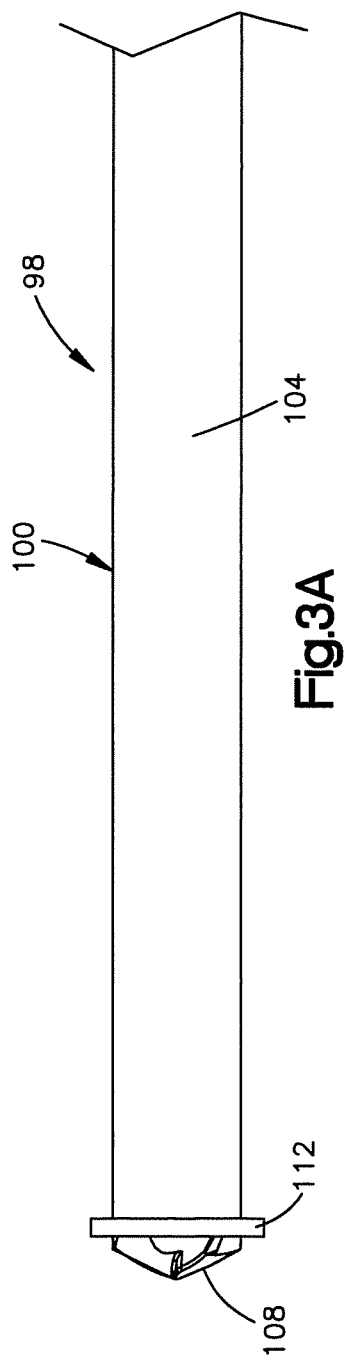
FIG. 3A is a side elevation view of a cutting tool system constructed in accordance with an embodiment, the cutting tool system including a first cutting tool that is configured to cut partially into the lamina to thereby form a hinge in the lamina as shown in FIG. 1C.

Referring now to FIG. 3A, the cutting tool system 98 is configured to cut into the posterior arch portion 26 of the vertebra, such as into the lamina 38. In accordance with the illustrated embodiment, the cutting tool system 98 includes a first cutting tool 100 that is configured to be inserted into the passageway 75 of the cannula 70 and advanced distally through the passageway 75 toward the vertebra such as toward the first portion 62 of the lamina 38 along the longitudinal axis C of the tube body 74. The first cutting tool 100 may be configured to cut into the lamina 38 to a certain depth so as to not cut all the way through the lamina 38. For example, the first cutting tool 100 may be a rotary tool such as a mill having a longitudinal body 104, a cutting tip 108 at a distal end of the body 104, and a stop member in the form of a shoulder 112 proximate to the cutting tip 108. The shoulder 112 can extend radially out from the tool body 104 at a location that limits the depth at which the cutting tool 100 can advance into the lamina 38. For example, the shoulder 112 can abut the lamina 38 so as to create an interference that prevents the first cutting tool 100 from advancing further into the lamina 38. Therefore during use, as the cutting tool 100 is advanced down the cannula 70, the cutting tip 108 cuts into the lamina 38 until the shoulder 112 abuts or otherwise engages an outer surface of the lamina 38. At this point, the first cutting tool 100 will no longer cut into the lamina 38 thereby preventing the cutting tool 100 from cutting all the way through the lamina 38. For instance, the cutting tool 100 can define a cutting depth between the shoulder 112 and the distal end of the cutting tip 108 that is between about 0.75 mm to about 1.25 mm, though it should be appreciated that the cutting depth can be sized as desired depending on the surgical procedure and the patient anatomy. Thus, the first cutting tool 100 can cut into, but not through, the lamina 38 so as to form the hinge 54 that is configured to open the lamina 38 in the manner described above. It should be appreciated, that one or more hinges 54 may be formed depending on what procedure is being performed. It should be further appreciated that the first cutting tool 100 can be configured to cut into, and entirely through, the lamina 38 on either side of the spinous process 42 as shown in FIG. 1B. Moreover, it should be appreciated that the first cutting tool 100 can be configured to cut into, and entirely through, the spinous process 42.

Once the hinge 54 has been created (if a hinge 54 is desired), then a second access path to the second portion 66 of the lamina 38 can also be created. The second access path may be created using the same methods and tools that are configured to create the first access path to the lamina 38. For example, the second access path may also be made using the access assembly 59 shown in FIGS. 2A and 2B. While the first access path was made to provide access to the first portion 62 of the lamina 38 located on a first side of the lamina 38, the second access path is made to provide access to a second portion 66 of the lamina 38 located on a second side of the lamina 38. That is, the first and second openings are configured to provide access to the lamina 38 on either side of the spinous process 42. As with the first access path, once the desired size (e.g., diameter) of the second access path is achieved, the cannula 70 can be slid over the dilators to thereby provide a minimally invasive work space for the second portion 66 of the lamina 38. It should be appreciated, however, that the access assembly 59 can include a second cannula so that two minimally invasive work spaces can be provided for the first and second portions of the lamina 38 at the same time.

Figure 3B:
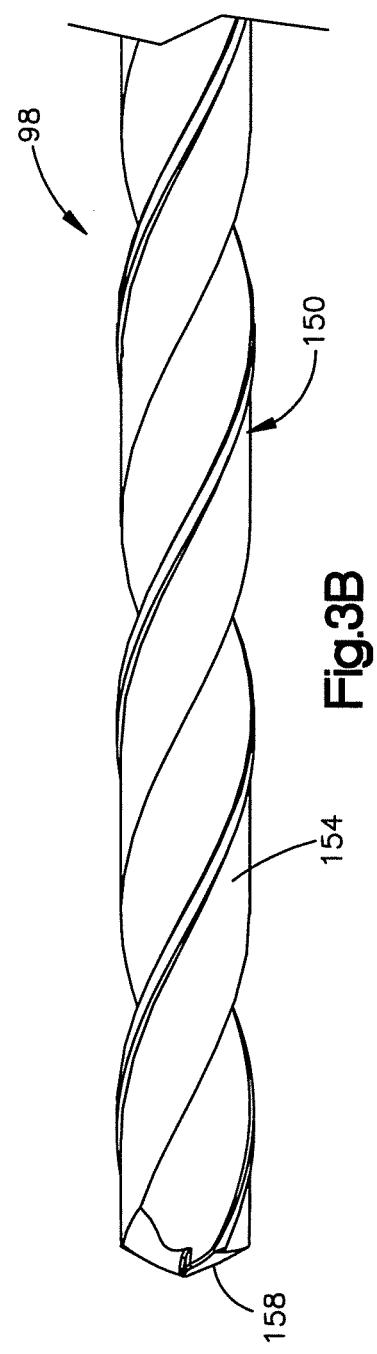
FIG. 3B is a side elevation view of the cutting tool system shown in FIG. 3A further including a second cutting tool configured to cut through the lamina or the spinous process to thereby form the implant receiving space.

As shown in FIG. 3B, the cutting tool system 98 can include a second cutting tool 150 that is configured to be inserted into the passageway 75 of the cannula 70 and is advanced toward the second portion 66 of the lamina 38 along the longitudinal axis C of the tube body. The second cutting tool 150 may be a rotary tool such as a mill having a longitudinal body 154, and a cutting tip 158 at a distal end of the body 154. The second cutting tool 150 may be coupled to the tube 70 outside of the access path so that the second cutting tool 150 can be advanced in precise increments. In this way the second cutting tool 150 will be able to cut completely through the lamina 38 to create an implant receiving space 46 of the lamina 38, while not inadvertently cutting the spinal cord. It should be appreciated that while the cutting tool system 98 is described as having first and second cutting tools 100 and 150, the cutting tool system 98 can include a single cutting tool that is configured to cut the lamina as described.

The cutting tool system 98, including the first and second cutting tools 100 and 150 can include an visualization device such as an endoscope. The endoscope can be attached to or separate from the first and second cutting tools 100 and 150. The endoscope can be configured to extend through passageway 75 along with the cutting tools 100 or 150 or can extend through the tissue external to the passageway 75.

Figure 4C:
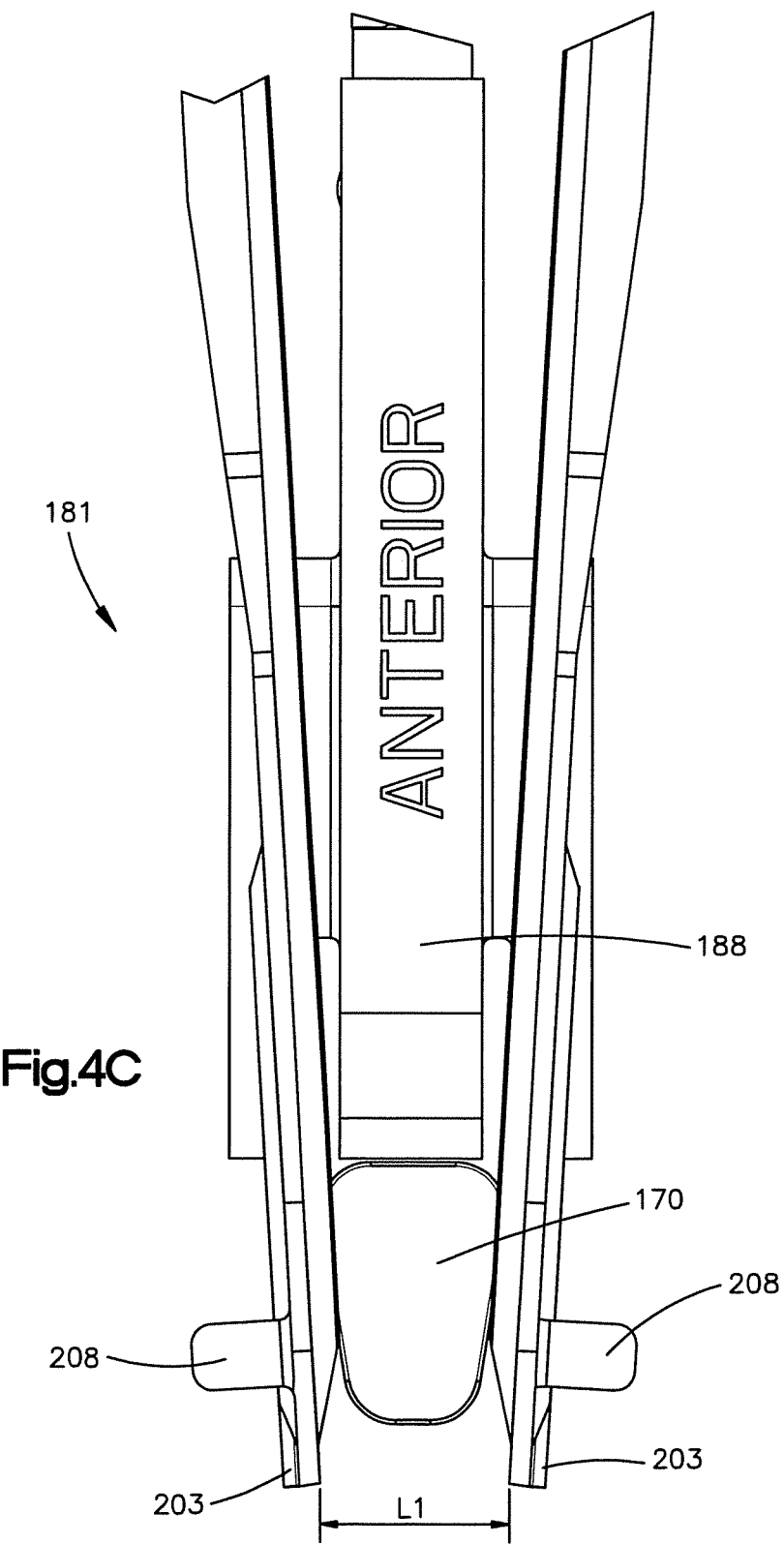
FIG. 4C is an expanded front elevation view of the distal portion of the implant inserter tool shown in FIG. 4B, the engagement portions of the spreading device having a first position whereby the engagement portions are separated by a first distance so as to be inserted into the implant receiving space.

Now referring to FIGS. 4A-4D, the implant assembly 181 includes an implant 170 and an inserter tool 180 that is configured to insert the implant 170 into the implant receiving space 46 of the lamina after the implant receiving space 46 has been created. For instance, after the implant receiving space 46 has been created, the second cutting tool 150 can be removed from the tube 70 and the inserter tool 180 and implant 170 can subsequently be advanced through the passageway 75 of the tube 70 toward the implant receiving space 46. Referring to FIG. 4A, the inserter tool 180 includes a housing 182 and an elongate pusher 184 that extends through the housing 182. The elongate pusher 184 includes a threaded rod 185, a handle 186 at a proximal end of the rod 185, and a biasing member 188 at a distal end of the rod 185 that is configured to either grip or push against the implant 170. The handle 186 may be any structure configured to be gripped by a user, while the biasing member 188 may be any structure capable of holding and/or pushing the implant 170. For example, in the illustrated embodiment, the biasing member 188 is an abutment surface 189 that is configured to push or otherwise move the implant 170 distally. It should be appreciated, however, that the biasing member 188 can include other configurations such as a threaded member, or a suction member so as to be able to grip and removeably affix the implant 170 to the inserter tool 180. The threaded rod 185 is configured to engage internal threads defined by the housing 182 such that the pusher 184 can be incrementally translated.

As shown, the implant assembly 181 can also include a spreading device 192 that extends distally from the housing 182 and around the implant 170. The spreading device 192 is configured to engage the implant receiving space 46 and then spread the posterior arch portion 26 such as the lamina 38 so as to expand or otherwise widen the implant receiving space 46 such that the implant 170 may be placed within the implant receiving space 46. The spreading device 192 includes a first arm 196 and a second arm 200 that extend distally from the housing 182 on opposite sides of the pusher 184. As shown, each arm 196 and 200 includes a first portion 201 that extends radially outward, away from the pusher 184, and a second angled portion 202 that extends radially inward toward the other of the angled portions 202. In this way, the first and second arms 196 and 200 curve around the implant 170, then toward each other until they terminate at a point distal to the implant 170. As shown, the arms 196 and 200 terminate such that the ends of the arms 196 and 200 are proximate to each other so as to be able to fit into and engage the implant receiving space 46 of the lamina 38. For example, the arms 196 and 200 can further include engagement portions 203 that extend from the second angled portions 202. The engagement portions 203 can be flat panels 205 that abut each other and are configured to engage the implant receiving space 46 of the posterior arch portion and provide a force direct or indirect against the posterior arch surfaces. For example, the engagement portions 203 can contact respective posterior arch surfaces to thereby widen the implant receiving space.

As shown, the first and second arms 196 and 200 each define a rail 206 that extends along a portion of the length of the arm toward the engagement portion 203. The rails 206 can be defined by the second angled portions 202 and the engagement portions 203 of the first and second arms 196 and 200 and are configured to guide the implant 170 and the biasing member 188 toward the engagement portions 203. In the illustrated embodiment, the rails 206 are slots 207 that extend through the arms 196 and 200 and are elongate along the length of the second angle portions 202. It should be appreciated, however, that the rails 206 can include other configurations as desired, so long as the rails are configured to guide the implant 170 toward the engagement portions 203.

As shown in FIG. 4B, the spreading device 192 further includes at least two stops 208 that extends laterally out from the engagement portions 203. The stops 208 are spaced from a distal end of the engagement portions 203 and are configured to limit the insertion depth of the engagement portions 203 into the implant receiving space 46. In the illustrated embodiment the stops 208 are projections that extend out from the engagement portions 203 on opposite sides of the rails 206.

As shown in FIGS. 4C and 4D, the spreading device 192 can have a first or engaging position as shown in FIG. 4C and a second or expanded position as shown in FIG. 4D. While in the first position, the engagement portions 203 are separated from each other by a first distance $L_1$ and while in the second position the engagement portions 203 are separated from each other by a second distance $L_2$ that is greater than the first distance $L_1$. It should be appreciated that while in the first position the engagement portions 203 can abut each other such that the first distance $L_1$ is 0 mm. As the implant 170 is guided down the rails 206 the implant 170 forces the engagement portions 203 away from each other to thereby increase the distance between the engagement portions 203 from the first distance to the second distance.

Now referring now to FIGS. 5A-5C the implant 170 includes an implant body 171 having a leading end 173a with respect to insertion into the implant receiving space 46, and a trailing end 173b opposite the leading end 173a with respect to a central longitudinal axis 177, opposed sides 175 that extend between the leading and trailing ends 173a and 173b, and opposed upper and lower surfaces 183a and 183b, respectively. The leading end 173a can define a different length than the trailing end 173b. For instance, the leading end 173a defines a length that is less than that of the trailing end 173b in accordance with the illustrated embodiment. Accordingly, the sides 175 can be tapered (or angularly offset with respect to the longitudinal axis 177) between the leading and trailing ends 173a and 173b. For instance, one or both of the sides 175 can be angled inwards (e.g., toward each other) along a direction from the trailing end 173b toward the leading end 173a. Thus, the implant body 171 can be generally wedge shaped, and configured to be inserted into the implant receiving space 46, such that the sides 175 are configured to abut complementary surfaces of the posterior arch portion 26 such as the lamina 38 that at least partially define the implant receiving space 46. In this way the sides 175 can define first and second bone engaging surfaces that are configured to urge against the first and second posterior arch surfaces. The implant 170 can further define at least one aperture 190 that extends into the body 171, for instance into the upper surface 183a toward the lower surface 183b (See FIG. 5D). The aperture 190 can further extend into one or both sides 175, such that bone growth promoting material can be added into the aperture 190, for instance in the upper surface 183a, once the implant 170 has been inserted into the implant receiving space 46. The bone growth promoting material can thus extend into the sides 175 within the aperture 190 so as to contact the opposed surfaces of the posterior arch that define the implant receiving space 46. For instance, the leading end 173a defines a length that is less than that of the trailing end 173*b* in accordance with the illustrated embodiment.

As shown in FIG. 5D, the implant can further include at least one tooth such as a plurality of teeth 179 that project out from the implant body 171, and in particular project out from the sides 175 and are configured to abut and enhance contact with the surfaces of the posterior arch that at least partially define the implant receiving space 46. Alternatively, the implant 170 can be inserted into an implant receiving space 46 of the type described above. Accordingly, after the implant 170 has been implanted and the other tools of the posterior arch expansion system have been removed, the implant 170 maintains the implant receiving space 46 at a width substantially equal to the width of the implant 170 that is configured to relieve impingement into the spinal canal. The implant can further define a lip 191 that overhangs at least one of up to all of the sides 175, the leading end 173*a*, and the trailing end 173*b*, and abuts the an outer surface of the posterior arch portion 26 when the implant body 171 is fully inserted in the implant receiving space 46.

Referring now to FIGS. 5A-5C, the implant 170 can alternatively or additionally include at least one such as two mating members 187 that project out one or both sides 175 of the implant body 171. The mating members 187 can be substantially dome-shaped or any suitable alternative shape as desired. The mating members 187 are configured to engage a respective rail 206 of the first and second arms 196 and 200 such that the implant 170 rides along the rails 206 as the implant is being advanced by the elongate pusher. Additionally, the mating members 187 can act as locking protrusions to lock the implant in the implant receiving space 46. Accordingly, a complementary aperture can be formed (e.g., cut) into, but not through, the posterior arch portion 26 at locations that are configured to receive and capture the mating members 187 of the implant 170 when the implant 170 is inserted into the implant receiving space 46.

Figure 6A:
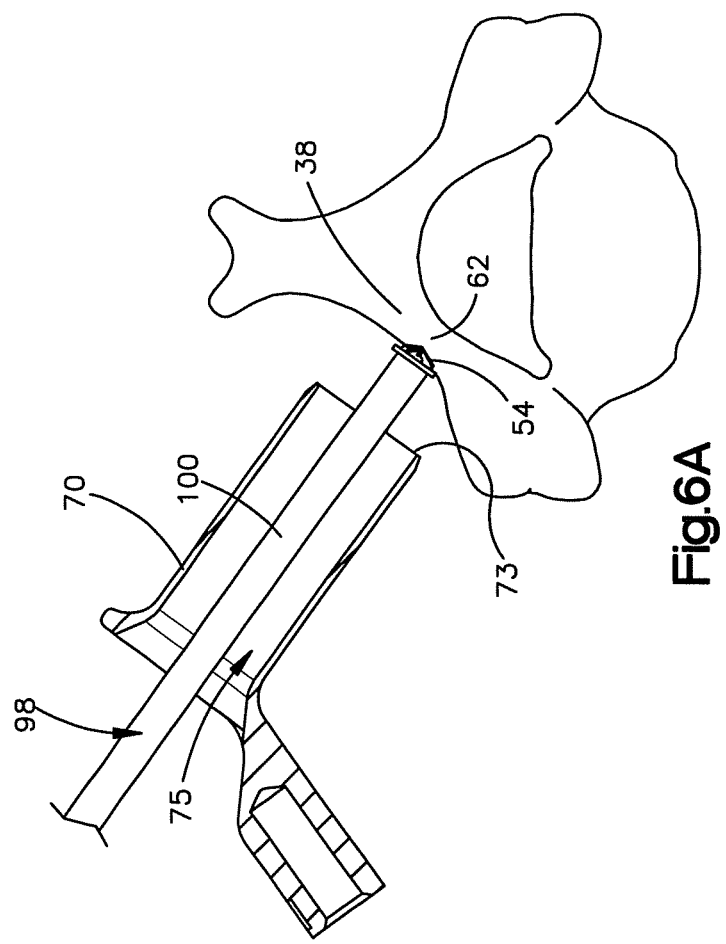
FIG. 6A is a top sectional view of the first cutting tool of the cutting assembly extending through the passageway of the cannula of the access assembly to thereby form the hinge in the first portion of the lamina.
Figure 6B:
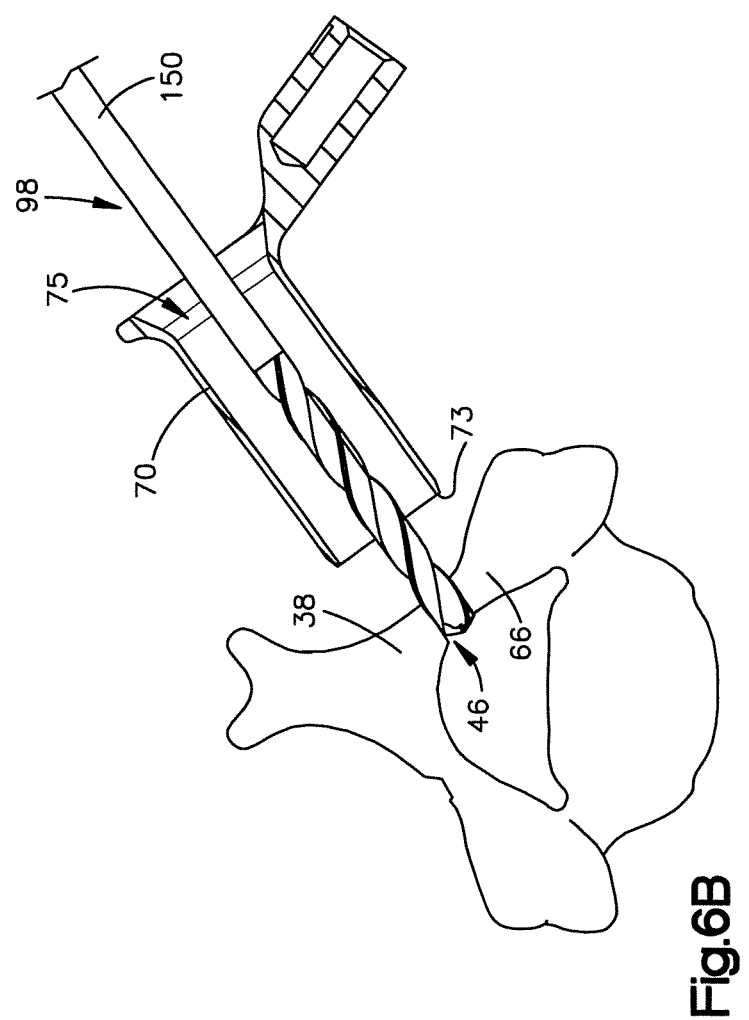
FIG. 6B is a top sectional view of the second cutting tool of the cutting assembly extending through the passageway of the cannula of the access assembly to thereby form the implant receiving space in the second portion of the lamina.

In operation and in reference to FIGS. 6A-6E, the access assembly 59 and in particular the cannula 70 is positioned such that the distal end 73 of the cannula 70 is proximate to the first portion of the lamina 38. The cutting tool system 98 can then be advanced through the passageway 75 of the cannula 70 toward the first portion 62 of the lamina 38. By activating the cutting tool system 98, the cutting tool system 98 can cut at least part way through the first portion 62 of the lamina 38 to form the hinge 54. Once the hinge 54 is formed, the access assembly 59 and in particular the cannula 70 can be positioned such that the distal end of the cannula 70 is proximate to the second portion 66 of the lamina 38 as shown in FIG. 6B. The cutting tool system 98 can then be advanced through the passageway 75 of the cannula 70 toward the second portion 66 of the lamina 38. By activating the cutting tool system 98, the cutting tool system 98 can cut completely through the second portion 66 of the lamina 38 to thereby form the implant receiving space 46.

Figure 6C:
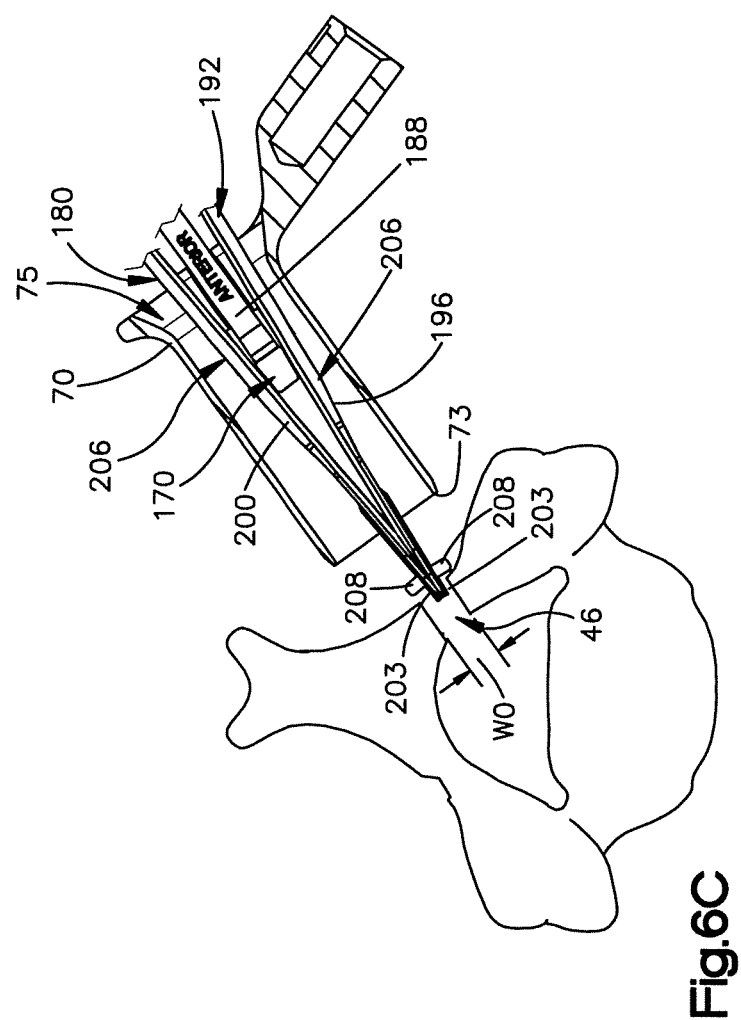
FIG. 6C is a top sectional view of the implant assembly extending through the passageway of the cannula of the access assembly such that the engagement portions of the inserter tool are inserted into the implant receiving space.
Figure 6D:
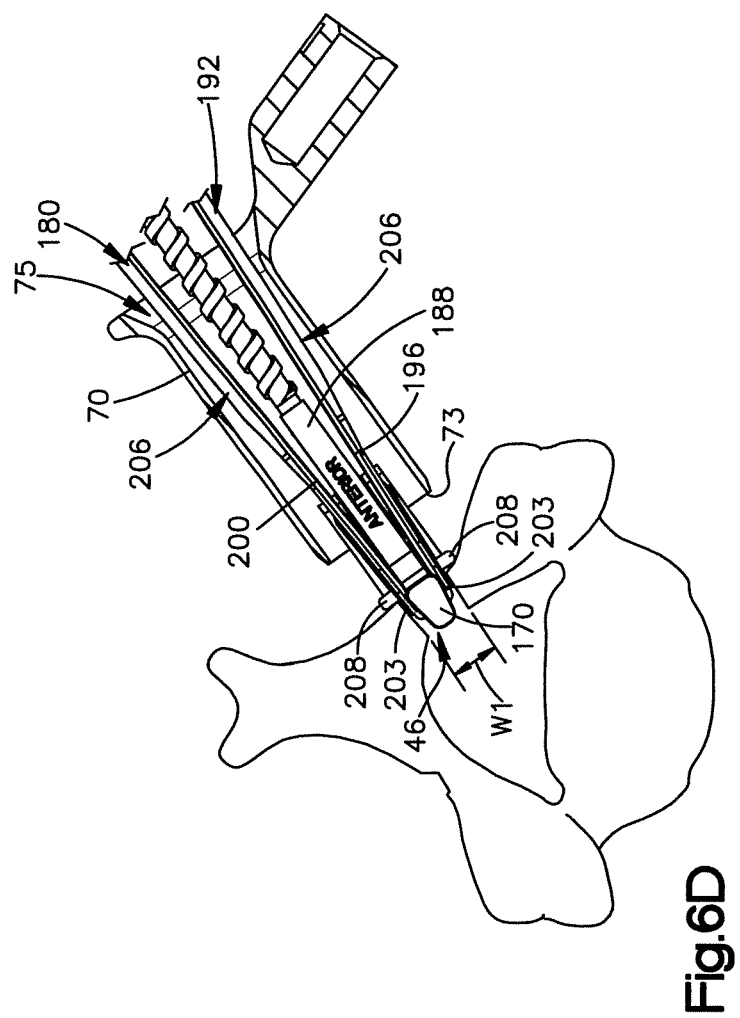
FIG. 6D is a top sectional view of the implant assembly after the implant has been advanced into the implant receiving space and the implant receiving space has been widened by the inserter tool.
Figure 6E:
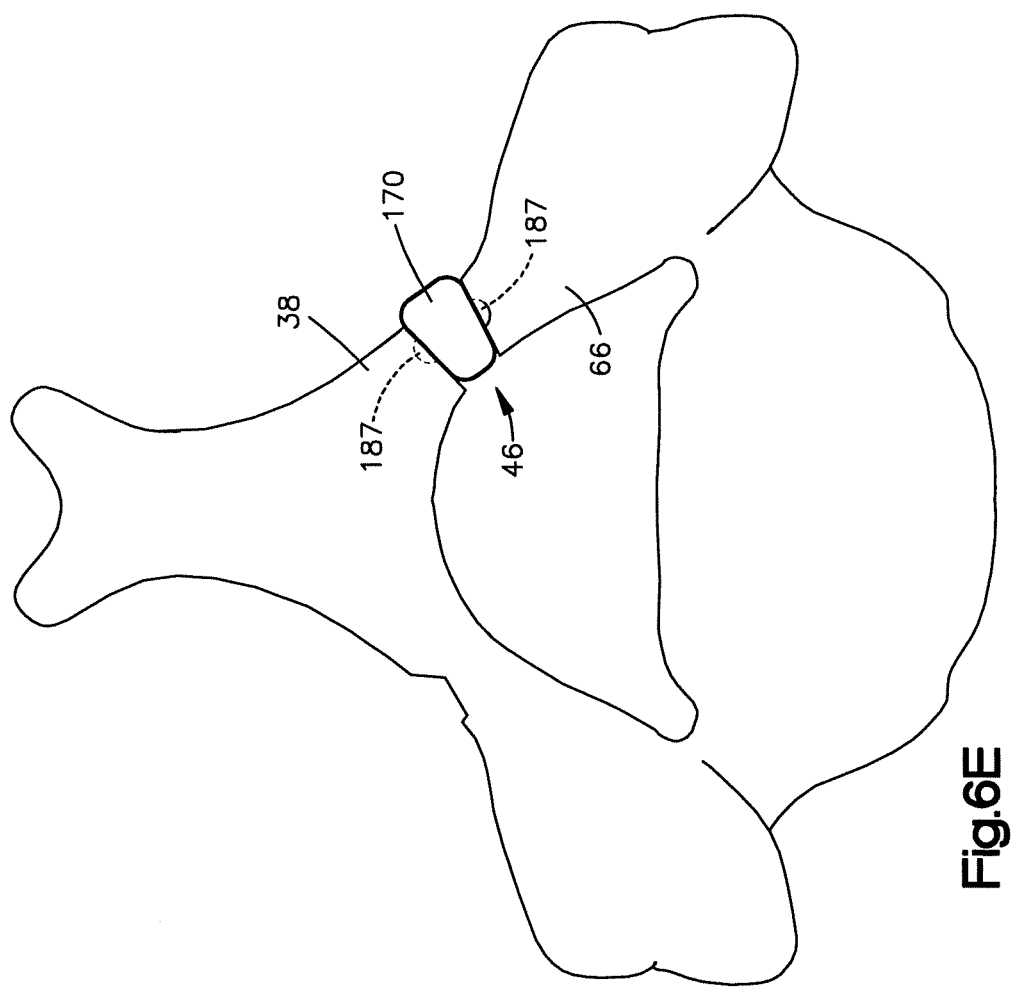
FIG. 6E is a top sectional view of the implant secured within the implant receiving space to thereby retain the widened implant receiving space in the widened position.

Now in reference to FIGS. 6C-6E, the inserter tool 180 with the implant 170 coupled to the inserter tool 180 can be is inserted into and advanced through the passageway of the cannula 70. The implant 170 can be coupled to the inserter tool 180 by engaging the mating members 187 of the implant 170 with the rails 206 of the first and second arms 196 and 200. As the inserter tool 180 is advanced further through the passageway 75 the engagement portions 203 of the arms 196 and 200 of the spreading device 192 engage the implant receiving space 46 of the lamina 38. By activating the pusher 184 so as to advance the implant 170 toward the implant receiving space 46, the implant 170 will contact and force or otherwise urge the arms 196 and 200 away from each other to thereby spread the implant receiving space 46 and expand the lamina 38, such that the implant receiving space 46 is moved from a first position whereby a distance measured between the opposed posterior arch surfaces has a first width, to a second position whereby the distance measured between the opposed posterior arch surfaces increases to a second width. As the implant 170 is advanced further, the implant receiving space 46 will spread to a size such that the implant 170 is placed within the implant receiving space 46 to thereby maintain the lamina 38 in its expanded or widened position. As will be described, the implant receiving space 46 may be further expanded or otherwise widened by expanding the implant 170 if the implant 170 is expandable. In such cases, the implant receiving space can be moved from a first position to a second position, whereby a distance between the posterior arch surfaces is increased, and then subsequently moved to a third position upon expansion of the implant whereby the distance between the posterior arch surfaces is further increased.

Finally, the inserter tool 180 can be disengaged from the implant 170 and removed from the cannula 70. As shown in FIG. 6E, the implant 170 may then be secured to the lamina 38 by having the mating members 187 of the implant 170 engage opposed cutouts in the lamina or with screws or other fastening devices. Because the procedure is performed using only the access path provided by the access assembly 59, the entire procedure is minimally invasive. Therefore, through an entirely minimally invasive procedure, a patient's lamina 38 may be expanded or otherwise widened from a first position to a second position so as to increase the size of the spinal canal and relieve the pressure on the patient's spinal cord.

It should be appreciated that the posterior arch expansion can be completed by cutting through the spinous process 42 as shown for example in FIG. 1D or by cutting two implant receiving spaces into the lamina for as shown in FIG. 1C. Such posterior arch expansion methods can be performed using similar methodology or steps as described in conjunction with FIGS. 6A-6E.

Now referring to FIGS. 7A-7C, the cutting tool system 98 can include other configurations that are configured to cut either part way through, or fully through the posterior arch portion 26. For example, the cutting tool system 98 can include a cutting tool that is provided as a mill as described above, an ultrasonic cutting tool 210 as shown in FIG. 7A, a wire saw 220 as shown in FIG. 7B, or a rib cutter 230 as shown in FIG. 7C. While the cutting tool system 98 has been described in accordance with certain embodiments, it should be appreciated that the posterior arch expansion system can include any alternative cutting tool assemblies suitable to cut a portion of the posterior arch.

Referring to FIG. 7A, the ultrasonic cutting tool 210 includes an elongate body 234 having a cutting tip 238. By applying ultrasonic shockwaves to the cutting tool 210, the cutting tip 238 will vibrate rapidly and cut through the posterior arch portion 26. As with the cutting tools shown in FIGS. 3A and 3B, the ultrasonic cutting tool 210 should be configured to fit within the tube 70. In operation, the ultrasonic cutting tool 210 is advanced toward the posterior arch portion 26 within the passageway of the tube 70 until the cutting tip 238 is abutting the posterior arch portion 26. When the ultrasonic cutting tool 210 is activated, the vibrating tip 238 will cut through the posterior arch portion 26.

Referring to FIG. 7B, the wire saw 220 includes a length of wire 242 having an abrasive surface 246. In operation, the wire 242 is advanced toward the posterior arch portion 26 through the passageway of the tube 70 to a location that is proximate to the posterior arch portion 26. The wire 242 is then threaded around the posterior arch portion 26 and back up the cannula 70 such that both ends of the wire 242 are extending proximally from the cannula 70. By oscillating the wire 242 back and forth, the abrasive surface 246 of the wire 242 will cut through the posterior arch portion 26.

Referring to FIG. 7C, the rib cutter 230 includes a body 250 having a cutting portion 254 at its distal end. The cutting portion 254 includes a distal sharp edge 258, a pusher 262 and a gap 266 defined between the edge 258 and the pusher 262. As shown, the sharp edge is curved and extends proximally toward the pusher 262, and the pusher 262 is configured to translate toward the sharp edge 258. In operation, the rib cutter 230 will be advanced down the tube 70 toward the posterior arch portion 26. The cutting portion 254 will be positioned such that the posterior arch portion 26 is received within the gap 266 with the sharp edge 258 abutting the back surface of the posterior arch portion 26 and the pusher 262 abutting the front surface of the posterior arch portion 26. Once properly positioned, the pusher 262 is translated forward to force the posterior arch portion 26 against the sharp edge 258. With further translation, the sharp edge 258 will cut through the posterior arch portion 26.

The posterior arch expansion system and in particular the implant assembly 181 can include any suitable implant that is configured to be advanced through a minimally invasive access path, such as through the access member 70, that provides the access path to the posterior arch portion 26, and expand the posterior arch. Because the implant or implants can be advanced down the access member 70, the fixation procedure can be referred to as minimally invasive. To place the implants within the implant receiving space 46 of the posterior arch, the implants may be inserted using the inserter tool 180 and spreading device 192 so as to widen the implant receiving space 46 during insertion, or the implants may have a first width when they are being inserted into the implant receiving space 46, and once inserted, the implants are expanded to a second width that is wider than the first width. It should thus be appreciated that the implant alone or in combination with the spreading device can expand the implant receiving space 46. Whether the spreading device 192 expands the implant receiving space 46 or the implant expands the implant receiving space 46, or both, it should be appreciated that the implants are inserted into the implant receiving space 46 using a minimally invasive procedure. Example implants that can be inserted through the minimally invasive access path such as the path 75 through the cannula 70 are described below. It should be appreciated, however, that the implant is not limited to those described, and that other configurations are envisioned.

In another embodiment and in reference to FIG. 8, the implant may include an engagement member that is configured to engage the posterior arch portion 26 by capturing outer surfaces of a respective portion of the posterior arch portion 26 when the implant is inserted within the implant receiving space 46 of the posterior arch portion 26. As shown, an implant 310 includes a body 314, and a pair of engagement members 316 that are each configured as a pair of wings 318 extending from opposed sides of the body 314. As shown, the implant body 314 has a width that is configured to maintain the implant receiving space 46 in the expanded position. Therefore, the implant 310 should be inserted using the inserter tool 180 so that the implant receiving space 46 can be widened to allow the implant 310 to be inserted within the implant receiving space 46 without interference from the posterior arch portion 26. Each pair of wings 318 includes first and second wings 322, 326 that extend out from opposed edges 330 of the body 314, and away from the body 314 at an angle toward the outside surfaces of the posterior arch portion 26. The first and second wings 322 and 326 of each pair of wings 318, therefore define a cavity 334 that is configured to receive a respective portion of the posterior arch portion 26 as shown in FIG. 8. Once the implant 310 is properly positioned within the implant receiving space 46 of the posterior arch portion 26, the wings 322 and 326 of each pair of wings 318 are fastened to the posterior arch portion 26 to thereby securely hold the implant 310 in place.

In another embodiment and in reference to FIG. 9, the implant can include an engagement member that is configured to clamp down against outer surfaces of respective portions of the posterior arch portion 26. As shown, an implant 360 includes a body 363 that is configured as a shaft 364, a first engagement member configured as a first disc 368 moveably attached to the shaft 364, and an opposed second engagement member configured as a second disc 372 fixed to a distal end of the shaft 364. The shaft 364 is threaded and has a diameter $D_1$ that is equal to the width in which the posterior arch portion 26 is to be expanded. It should be appreciated, however, that the implant 360 could include a sleeve having a diameter $D_1$ that is placed over the shaft 364 and between the first and second discs 368 and 372. In either case, the implant 360 should be inserted using the inserter tool 180 so that the implant receiving space 46 can be widened to allow the implant 360, or at least the shaft 364 to be inserted within the implant receiving space 46 without interference from the lamina.

The shaft 364 includes threads 376 that are configured to engage threads defined by a bore 384 that extends through a center of the first disc 368. The threaded engagement between the shaft 364 and the first disc 368 allows the first disc 368 to be incrementally translated toward the second disc 372. As shown, the first and second discs 368 and 372 include teeth 388 that extend from opposed internal surfaces 392 of the discs 368 and 372. In operation the implant 360 is placed such the shaft 364 is located within the implant receiving space 46 and the first and second discs 368 and 372 are located on opposed sides of the posterior arch portion 26. Once the implant 360 is properly positioned within the implant receiving space 46 of the posterior arch portion 26 the first disc 368 may be translated toward the second disc 372 until the teeth 388 of the two discs 368 and 372 engage the outer surfaces of the posterior arch portion 26 to thereby clamp the implant 360 to the posterior arch portion 26. Once the teeth 388 have engaged the posterior arch portion 26, the implant 360 is securely held in place.

In another embodiment and in reference to FIGS. 10A and 10B, the implant may be a rivet that clamps against the posterior arch portion 26 to hold the implant in place. As shown, an implant 410 includes a body configured as a shaft 414, a first engagement member configured as a head 418 and attached to a proximal end of the shaft 414, and a mandrel 422 that extends through the center of both the first head 418 and the shaft 414. The shaft 414 has a diameter $D_1$ that is equal to the width in which the posterior arch portion 26 is to be expanded. Therefore, the implant 410 should be inserted using the inserter tool 180 so that the implant receiving space 46 can be widened to allow the implant 410, or at least the shaft 414, to be inserted within the implant receiving space 46 without interference from the posterior arch portion 26.

In operation, the implant 410 is placed such that the first head 418 abuts the outer surfaces of the posterior arch portion 26, and a majority of the shaft 414 extends into the implant receiving space 46, with a portion 426 of the shaft 414, known as the blind end, protruding into the spinal canal. Once properly positioned, the mandrel 422 is drawn proximally to thereby expand the portion 426 of the shaft 414 within the spinal canal, and create a second engagement member configured as a head 430 that abuts the posterior arch portion 26 within the spinal canal, as shown in FIG. 10B. The first and second heads 418 and 430 clamp the implant 410 to the posterior arch portion 26 to thereby securely hold the implant 410 in place.

The implant can also be configured to expand along a direction that is transverse to the direction in which the implant is inserted into the implant receiving space. That is, if the implant is in inserted into the implant receiving space along an insertion direction, the implant can then be subsequently expanded along an expansion direction that is transverse to, such a substantially perpendicular to, the insertion direction. FIGS. 11A-19B disclose several embodiments of an implant that can expand from a first or compressed configuration or position to a second or expanded configuration or position.

For example and in reference to FIGS. 11A and 11B, the implant can include a body that is configured to expand from a first or compressed configuration or position to a second or expanded configuration or position, thereby expanding the implant receiving space after the implant has been implanted. For instance, referring to FIG. 11A, an implant 450 includes an expandable body 454, and a respective engagement member 455 that extends from opposed ends of the body 454. The expandable body 454 includes a first threaded member 456 that extends from a first engagement member 455 and a second threaded member 457 that extends from a second engagement member 455. The first threaded member 456 includes left handed threads while the second threaded member 457 includes right handed threads. The second threaded member 457 further defines an internal bore 470 that is configured to receive the first threaded member 456 when the implant is in the compressed configuration or position. The expandable body 454 further includes an expansion mechanism 458 that defines a threaded bore 459. Each of the first and second threaded members 456 and 457 engage an opposed end of the threaded bore 459 such that rotation of the expansion mechanism 458 causes the first and second threaded members 456 and 457 to translate away from each other. As shown, when the expansion mechanism 458 is actuated both the implant 450 and the implant receiving space expand from an initial first width $W_0$, as shown in FIG. 11A, to an expanded second width $W_1$, as shown in FIG. 11B.

The body 454 further defines first and second opposed bone contacting surfaces 466a and 466b that are configured to engage the first and second posterior arch surfaces. When the body 454 is expanded from the first width to the second width, the first and second bone contacting surfaces 466a and 466b urge against the first and second posterior arch surfaces to thereby expand or otherwise widen the implant receiving space 46.

The engagement members 455 may have a variety of configurations so long as they are capable of engaging the lamina to thereby hold the implant 450 in place. For example, the engagement members 455, in the illustrated embodiment include fixation element receiving apertures 460 configured to receive fixation elements such as bone screws. The screws will engage the lamina to thereby fasten the implant 450 to the lamina.

In operation, the implant 450 is passed through the passageway of the cannula 70 and subsequently inserted into the implant receiving space 46 while the body 454 is in the compressed configuration or position and the implant defines the first width $W_0$. Once properly placed, the engagement members 455 may be fastened to the lamina with bone screws and the expansion mechanism 458 may be actuated to allow the body 454 to expand such that the implant 450 and the implant receiving space expand to the second width $W_1$. The expansion mechanism 458 can be activated using a tool that extends through passageway of the cannula and engages the expansion mechanism 458 so as to rotate the expansion mechanism. For example, the expansion mechanism 458 can have a rough outer surface that allows the tool to engage the expansion mechanism to thereby rotate the expansion mechanism.

Figure 12A:
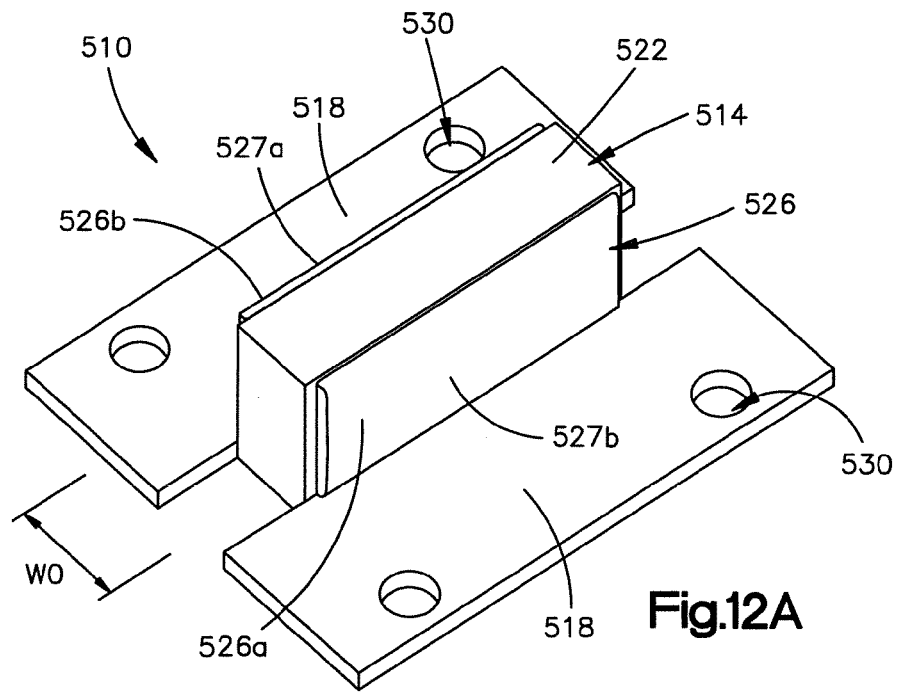
FIG. 12A is a perspective view of an implant constructed in accordance with another embodiment, the implant including an expandable body that has a balloon such that expansion of the balloon causes the implant to expand.
Figure 12B:
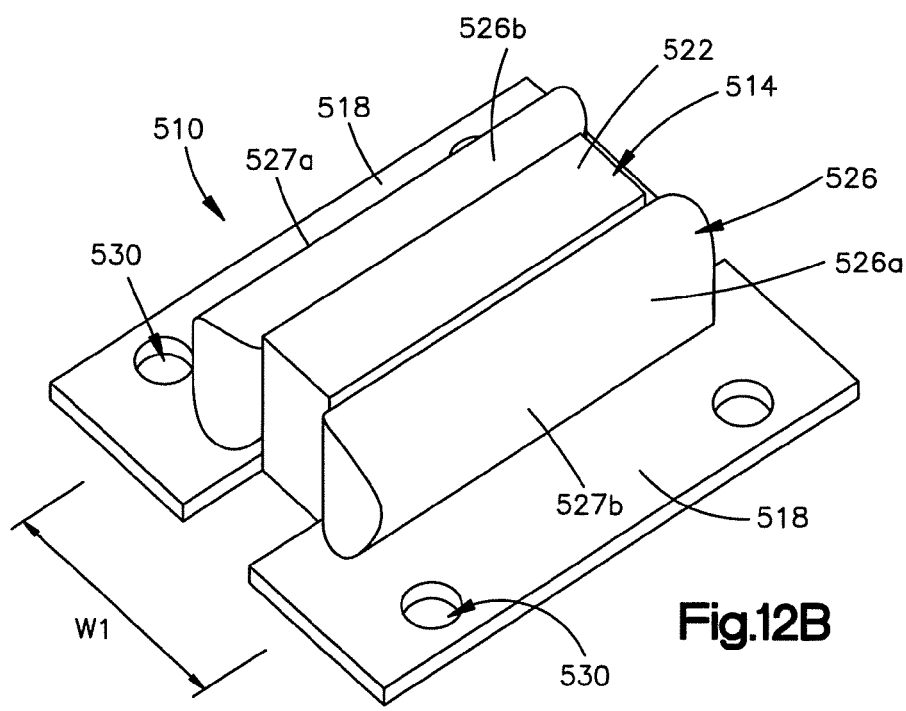
FIG. 12B is a perspective view of the implant shown in FIG. 12A in an expanded configuration or position.

In another embodiment and in reference to FIGS. 12A and 12B, the implant may be expanded using an inflatable device from the first or compressed configuration or position to the second or expanded configuration or position. As shown, an implant 510 includes an expandable body 514 and engagement members 518 that extend from opposed sides of the body 514. The body 514 includes a frame 522 and at least one expandable balloon 526 having laterally opposed sides 526a and 526b that extend through the frame 522. The balloon 526 is configured to inflate to thereby expand the implant 510 from a defined initial first width $W_0$, as shown in FIG. 12A, to an expanded second width $W_1$, as shown in FIG. 12B. The balloon 526 can be inflated by injection of any suitable expansion media into the balloon 526. For instance, cement can be pumped through a cannulated rod that is attached to the frame 522 and in fluid communication with the interior of the balloon.

The body 514 and in particular the opposed sides of the balloon 526a and 526b, further define first and second opposed bone contacting surfaces 527a and 527b that are configured to engage the first and second posterior arch surfaces. When the body 514 is expanded from the first width to the second width, the first and second bone contacting surfaces 527a and 527b urge against the first and second posterior arch surfaces to thereby expand or otherwise widen the implant receiving space 46.

The engagement members 518 may have a variety of configurations so long as they are capable of engaging the lamina to thereby hold the implant 510 in place. For example, the engagement members 518, in the illustrated embodiment, each define a plate that includes fixation element receiving apertures 530 configured to receive fixation elements such as bone screws. The screws will engage the lamina to thereby fasten the implant 510 to the lamina.

In operation, the implant 510 is inserted into the implant receiving space 46 while the body 514 is compressed and the implant 510 defines the first width $W_0$. The initial first width $W_0$ therefore is less than or substantially equal to the width of the implant receiving space 46, and is accordingly small enough to allow the implant 510 to be inserted within the implant receiving space 46. Once properly placed, the balloon 526 may be inflated to thereby expand the implant receiving space 46. In other words, expansion of the balloon 526 expands the implant receiving space 46 from a first width (which is substantially equal to the first width $W_0$ defined by the implant 510) to a second width (which is substantially equal to the second width $W_1$ defined by the implant 510). Therefore, the implant 510 can be said to expand the implant receiving space 46 from a first width to a second expanded width. While being inflated, the frame 522 will orient the balloon expansion, preventing it from expanding against the dura and orienting it towards the lamina. Once the lamina has been expanded, the engagement members 518 may be fastened to the lamina. Otherwise stated, the frame 522 defines a guide that directs the expansion of the balloon 526 toward the lamina.

Figure 13:
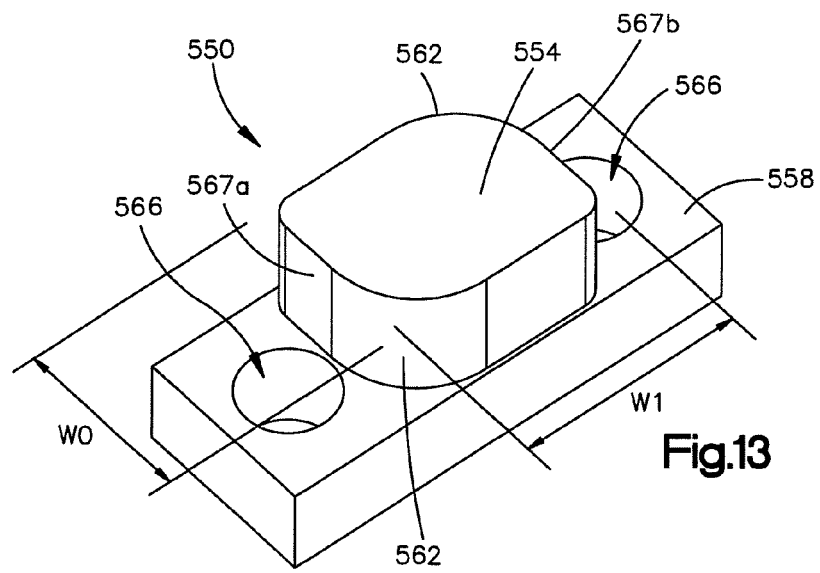
FIG. 13 is a perspective view of an implant constructed in accordance with another embodiment, the implant including an oblong body and is expandable such that when inserted into the implant receiving space of the posterior arch portion, the implant may be rotated to thereby widen the spinal canal.

In another embodiment and in reference to FIG. 13, the implant may be configured to rotate to thereby expand the lamina. As shown, an implant 550 includes an expandable body 554 and an engagement member 558 extending from the body 554. The body 554 is oblong and includes opposed rounded corners 562. As shown, the body 554 has a height that defines an initial first width $W_0$ and a length that defines a second expanded width $W_1$. The second width $W_1$ is greater than the first width $W_0$. The engagement member 558 defines a pair of opposed fixation element receiving apertures 566, each configured to receive a fixation element such as a bone screw. The body 554 is positioned on the engagement member 558 between the apertures 566 such that the second width $W_1$ extends from one aperture 566 to the other aperture 566.

The body 554 further defines first and second opposed bone contacting surfaces 567a and 567b that are configured to engage the first and second posterior arch surfaces. When the body 554 is expanded from the first width to the second width, the first and second bone contacting surfaces 567a and 567b urge against the first and second posterior arch surfaces to thereby expand or otherwise widen the implant receiving space 46.

In operation, the implant 550 is inserted into the implant receiving space 46 while in the first configuration or position such that the body 554 is oriented to have its first width $W_0$ within the implant receiving space 46. The initial first width $W_0$ therefore is less than or substantially equal to the width of the implant receiving space 46, and is accordingly small enough to allow the implant 550 to be inserted within the implant receiving space 46. By rotating the implant 550 90 degrees, the implant will be in the second configuration or position such that the body will be oriented to have its second expanded width $W_1$ within the implant receiving space 46. The rounded corners 562 of the body 554 allow the implant 550 to more easily force the opposed lamina portions apart. As shown, the expanded second width $W_1$ should be equal to the width in which the posterior arch portion 26 is to be expanded. Therefore, the implant 550 can be said to expand the implant receiving space 46 from a first width to a second expanded width.

Figure 14A:
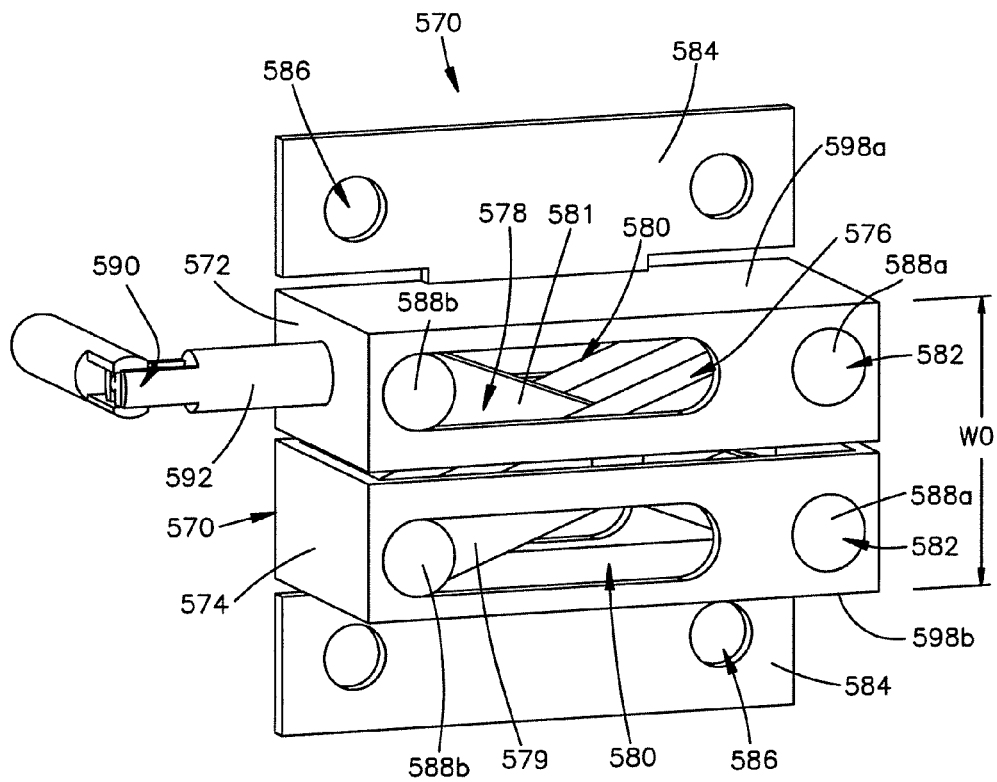
FIG. 14A is a perspective view of an implant constructed in accordance with another embodiment, the implant including an expandable body having first and second frames coupled together by first and second members, an expansion mechanism coupled to one of the members, such that rotation of the expansion mechanism causes the frames to move away from each other and the implant to expand.
Figure 14B:
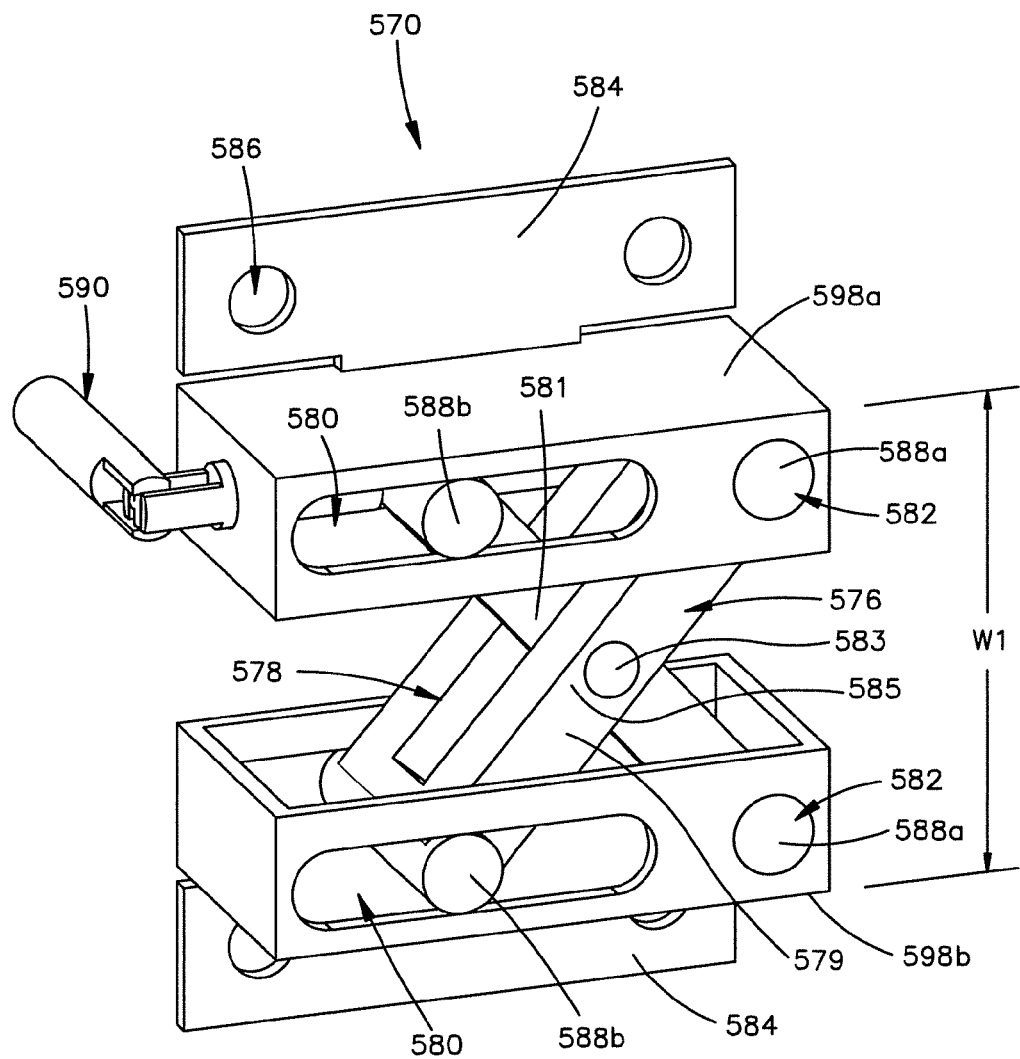
FIG. 14B is a perspective of the implant shown in FIG. 14A in an expanded configuration or position.

In another embodiment and in reference to FIGS. 14A and 14B, the implant may be configured to expand upon rotation of a wrench from the first or compressed configuration or position to the second or expanded configuration or position. As shown, an implant 570 includes a body 571 having first and second frames 572, and 574 that are connected by first and second members 576 and 578. As shown, each frame 572 and 574 defines an elongate channel 580 and a bore 582. The implant 570 further includes a respective engagement member 584 that extends from each frame 572 and 574. Each engagement member 584 defines a pair of fixation element receiving apertures 586 configured to receive screws to thereby fasten the implant 570 to the lamina. Each member 576 and 578 includes a respective elongate body 579 and 581 and first and second transverse rods 588a and 588b that extend outward from opposed ends of the elongate bodies 579 and 581. The first transverse rod 588a of the first member 576 extends into the bore 582 of the first frame 572, and the second transverse rod 588b of the first member 576 extends into the channel 580 of the second frame 574. Similarly, the first transverse rod 588a of the second member 578 extends into the bore 582 of the second frame 574, and the second transverse rod 588b of the second member 578 extends into the channel 580 of the first frame 572. The implant 570 can further include a transversal pin 583 that pivotally connects members 578 and 576 at a joint 585. During use, the first and second members 576 and 578 are pivotal with respect to the frames 572 and 574, respectively about their respective first transverse rods 588a, and are further configured to translate with respect to the frames 578 and 576, respectively, as their respective second transverse rods 588b ride along the complementary channels 580.

The implant 570 further includes a wrench 590 having a threaded member 592 that extends through a longitudinal threaded bore 594 of the first frame 572. As shown, the threaded member 592 is coupled to an end of the second member 578. As the wrench 590 is rotated, the threaded member 592 will translate into the first frame 572 and push the end of the second member 578. As the second member 578 is pushed, the rods 588 of the members 576 and 578 translate within their respective channels 580, and the members 576 and 578 rotate about their respective other rods 588 to thereby expand the implant 570. The pin 583 allows the rotation of each member 576 and 578 is equal, and both engagement members 584 translate substantially parallel to each other. As shown, the implant 570 may expand from an initial first width $W_0$, as shown in FIG. 14A, to an expanded second width $W_1$, as shown in FIG. 14B.

The body 571 and in particular the first and second frames 572 and 574 further define first and second opposed bone contacting surfaces 598a and 598b that are configured to engage the first and second posterior arch surfaces. When the body 571 is expanded from the first width to the second width, the first and second bone contacting surfaces 598a and 598b urge against the first and second posterior arch surfaces to thereby expand or otherwise widen the implant receiving space 46.

In operation, the implant 570 is inserted into the implant receiving space 46 such that the frames 572 and 574 are collapsed and the implant 570 defines the first width $W_0$. The initial first width $W_0$ therefore is less than or substantially equal to the width of the implant receiving space 46, and is accordingly small enough to allow the implant 570 to be inserted within the implant receiving space 46. Once the implant 570 is positioned and affixed to the lamina, the implant may be expanded to the expanded configuration or position. Therefore, by rotating the wrench 590, the frames 572 and 574 move away from each other to thereby expand the implant 570 such that the implant 570 defines the second width $W_1$. As shown, the expanded second width $W_1$ should be equal to the width in which the posterior arch portion 26 is to be expanded. Therefore, the implant 570 can be said to expand the implant receiving space 46 from a first width to a second expanded width.

Figure 15A:
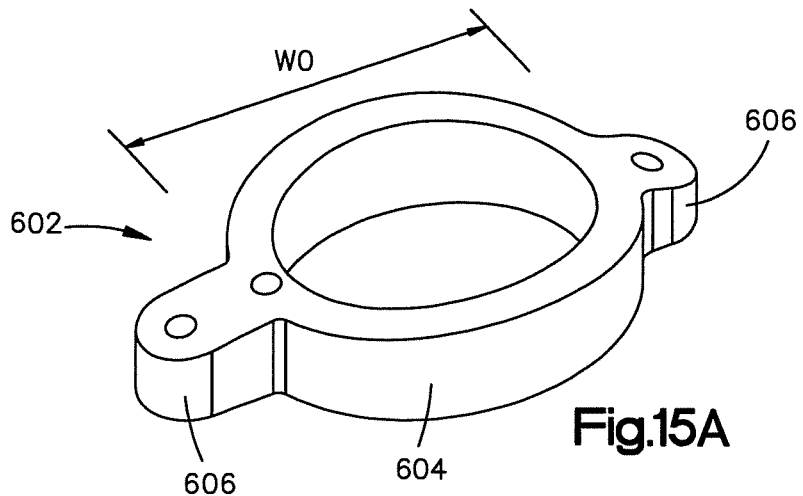
FIG. 15A is a perspective view of an implant constructed in accordance with another embodiment, the implant including an expandable body defined as a deformable O-ring such that compression of the O-ring causes the implant to expand.
Figure 15B:
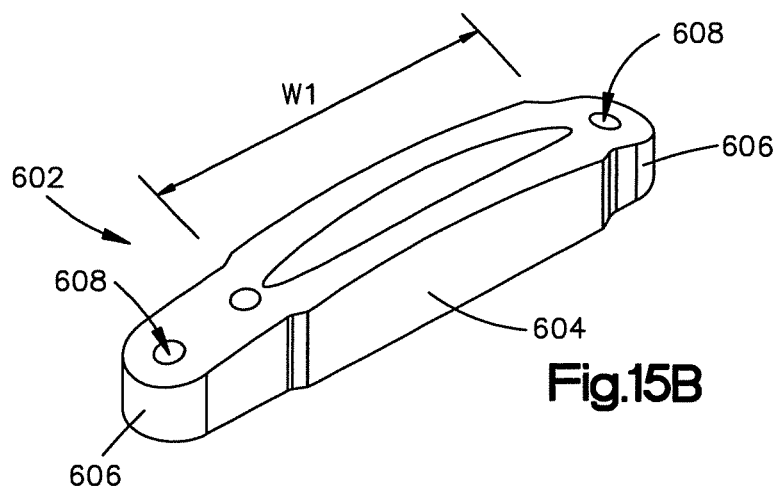
FIG. 15B is a perspective view of the implant shown in FIG. 15A in a flattened or expanded configuration or position.

In another embodiment and in reference to FIGS. 15A and 15B, the implant may be deformable from the first configuration or position to the second configuration or position. As shown, an implant 602 may include an expandable body 604 that defines an O-ring. The body 604 is made from a material that is capable of deforming. The implant 602 further includes opposed engagement members 606 that extend from the body 604. One of the engagement members 606 defines a fixation element receiving aperture 608, and the other engagement member 606 defines two fixation element receiving apertures 608. As shown in FIG. 15A, the body 604 initially defines an O-shape such that the implant 602 defines an initial first width $W_0$. As shown in FIG. 15B, the body 604 may be flattened or otherwise deformed to expand such that the implant 602 defines a second expanded width $W_1$.

In operation, the implant 602 is positioned and loosely affixed to the lamina by inserting a screw through bore 608 of the engagement member 606. The implant 602 is then rotated and positioned such that the other engagement member 606 may affixed to the lamina with second and third screws. Once the implant 602 is securely fastened to the lamina, the body 604 may flattened or otherwise deformed to thereby expand the implant and thus the lamina. Therefore, the implant 602 can be said to expand the implant receiving space 46 from a first width to a second expanded width.

Figure 16:
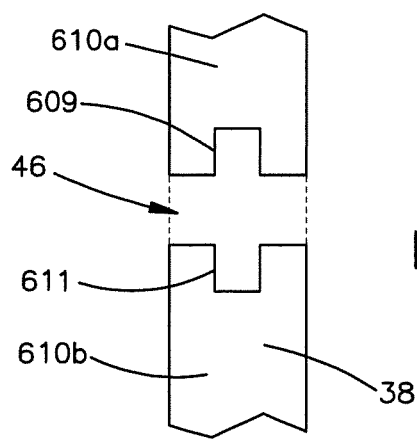
FIG. 16 is a schematic view showing a lamina cut so as to provide an implant receiving space that defines a pair of keel cuts extending into the posterior arch portion.

As shown in FIG. 16, the posterior arch portion 26 may be cut such that the posterior arch surfaces have other configurations. For example, posterior arch surfaces or the implant receiving space 46 can define two opposed keel cuts in the posterior arch portion 26. In particular, the implant receiving space 46 may include a first keel cut 609 defined in a first side 610a of the implant receiving space 46, and a second keel cut 611 defined in an opposed second side 610b of the implant receiving space 46. The first and second keel cuts 609 and 611 may be configured to receive first and second keels of an implant. It should be appreciated that the posterior arch surfaces can also define teeth or steps, for example.

In that regard, and in reference to FIGS. 17A and 17B, the implant may include keels that securely hold the implant within the implant receiving space 46 of the posterior arch portion 26. As shown, an implant 612 includes an expandable body 614 that defines a cavity 618, and includes a rotating member 622 mounted within the cavity 618 of the body 614. The body 614 further includes opposed first and second body portions 626 and 628 that are each configured to engage respective portions of the posterior arch portion 26. Each body portion 626 and 628 defines an internal surface 630 and an outer surface 634. Each body portion 626 and 628 of the body 614 further includes ratchet teeth 638 that extend from their respective internal surfaces 630 and toward the other body portion 626 and 628 of the body 614. The ratchet teeth 638 of the first body portion 626 have an engagement surface 642, while the ratchet teeth 638 of the second body portion 628 have an engagement surface 642 that is opposite to the engagement surface of the first body portion 626. In other words, the engagement surfaces 642 of the first body portion's 626 ratchet teeth are angled in a first direction, while the engagement surfaces 642 of the second body portion's 628 ratchet teeth are angled in a second direction that is opposite to the first direction. Each body portion 626 and 628 further includes an engagement member defined as a keel 646 that extends from its respective outer surface 634. The keels 646 are configured to engage keel cuts such as keel cuts 609 and 611 shown in FIG. 14 and therefore can be said to define engagement members.

The rotating member 622 includes a body 650 having a length L and opposed first and second angled ends 654 and 656. The ends 654 and 656 include ratchet teeth 658 having an engagement surface 662. As shown, the engagement surfaces 662 of the first end's 654 ratchet teeth 658 are angled in a first direction, while the engagement surfaces 662 of the second end's 656 ratchet teeth 658 are angled in a second direction that is opposite to the first direction. The rotating member 622 is configured to rotate through at least an arc of 90 degrees from a first position in which the implant 612 defines an initial first width $W_0$, to a second expanded position in which the implant 612 defines an expanded second width $W_1$.

The body 614 and in particular the first and second body portions 626 and 628 further define first and second opposed bone contacting surfaces 666a and 666b that are configured to engage the first and second posterior arch surfaces. When the body 614 is expanded from the first width to the second width, the first and second bone contacting surfaces 666a and 666b urge against the first and second posterior arch surfaces to thereby expand or otherwise widen the implant receiving space 46.

In operation, the implant 612 is inserted into the implant receiving space 46 while the rotating member 622 is in the first position and the implant 612 defines the first width $W_0$. The initial first width $W_0$ therefore is less than or substantially equal to the width of the implant receiving space 46, and is accordingly small enough to allow the implant 610 to be inserted within the implant receiving space 46. Once properly placed, the keels 646 are engaged with the first and second keel cuts 609 and 611, and the rotating member 622 may be rotated to its second position, so as to allow the body 614 to expand such that the implant 612 defines the expanded second width $W_1$. As the rotating member 622 is rotated (counter clockwise for the embodiment shown), the engagement surfaces 662 of the first end's ratchet teeth 658 are forced against the engagement surfaces 642 of the first body portion's ratchet teeth 638, and the engagement surfaces 662 of the second end's ratchet teeth 658 are forced against the engagement surfaces 642 of the second body portion's ratchet teeth 638. As the rotating member 622 is further rotated, the ratchet teeth of the rotating member 622 and the ratchet teeth of the body portion's 626 and 628 engage each other to thereby force the body portion's 626 and 628 apart. Once fully apart, the ratchet teeth lock the implant in the expanded second position which defines the second width $W_1$. As shown, the expanded second width $W_1$ should be equal to the width in which the posterior arch portion 26 is to be expanded. Therefore, the implant 612 can be said to expand the implant receiving space from a first width to a second expanded width.

Figure 18A:
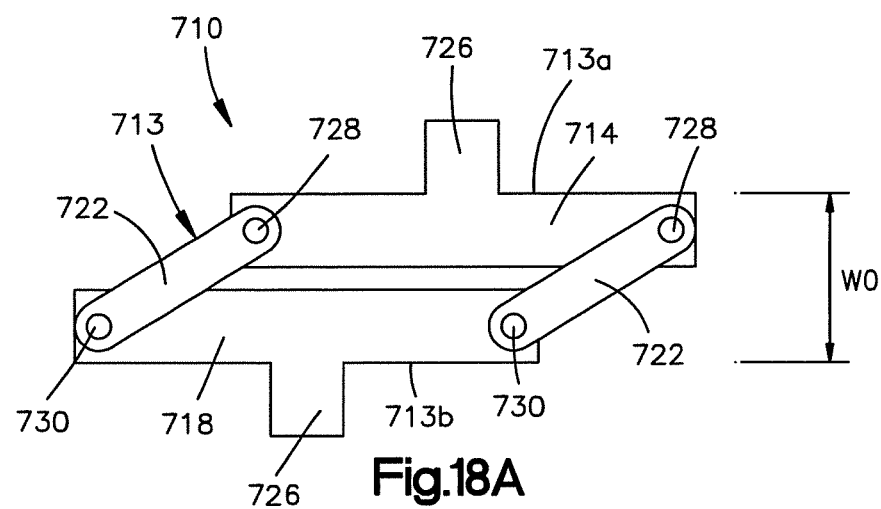
FIG. 18A is a side elevation view of an implant constructed in accordance with another embodiment, the implant including engagement members configured as keels capable of engaging the keel cuts defined by the implant receiving space of the posterior arch portion shown in FIG. 16, the implant further including first and second body portions coupled together by a pair of rotating members such that translation of the first body portion with respect to the second body portion causes the implant to expand.
Figure 18B:
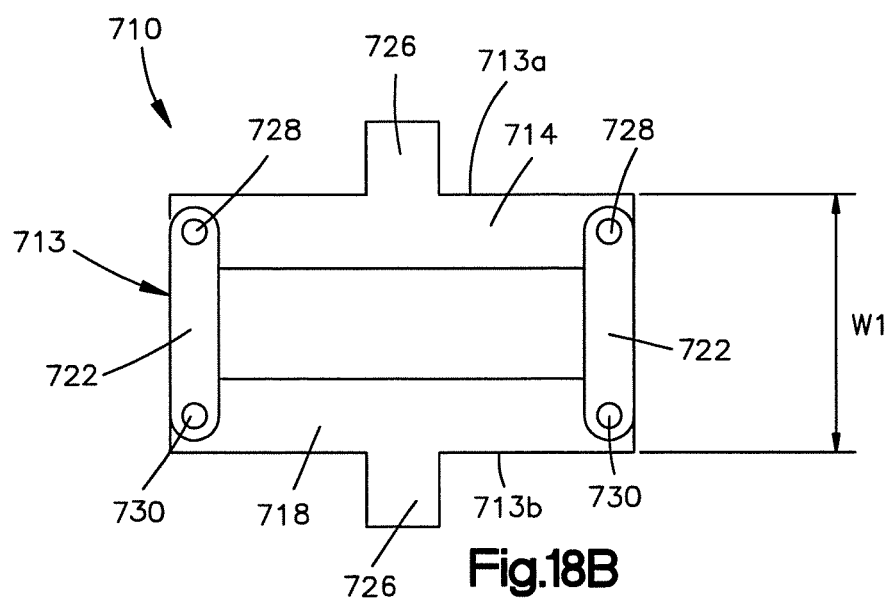
FIG. 18B is a side elevation view of the implant shown in FIG. 18A in an expanded configuration or position.

In another embodiment and in reference to FIGS. 18A and 18B, the implant may include rotating members coupled to both body portions and are configured to expand the implant upon translation of one of the body portions relative to the other. As shown, an implant 710 include a body 713 having a first body portion 714, an opposed second body portion 718 and at least two rotatable members 722 rotatably coupled or hinged to the first and second body portions 714 and 718. As shown, each body portion 714 and 718 includes a keel 726 that extends out from an outer surface of a respective body portion 714 and 718. The keels 726 are configured to engage the keel cuts 609 and 611 formed in the implant receiving space 46 of the posterior arch portion 26 and therefore can be said to define engagement members. The members 722 are each rotatably coupled to the first and second body portions 714 and 718 proximate to opposed ends of the body portions 714 and 718 at respective first and second pivots 728 and 730. The implant 710 is configured to expand from an initial first width $W_0$, to an expanded second width $W_1$, by rotating the first body portion 714 counter clockwise.

The body 713 and in particular the first and second body portions 714 and 718 further define first and second opposed bone contacting surfaces 731a and 731b that are configured to engage the first and second posterior arch surfaces. When the body 713 is expanded from the first width to the second width, the first and second bone contacting surfaces 731*a* and 731*b* urge against the first and second posterior arch surfaces to thereby expand or otherwise widen the implant receiving space 46.

In operation, the implant 710 is inserted into the implant receiving space 46 while the implant 710 is in its first position and defines the first width $W_0$. The initial first width $W_0$ therefore is less than or substantially equal to the width of the implant receiving space 46, and is accordingly small enough to allow the implant 710 to be inserted within the implant receiving space 46 without first expanding the implant receiving space 46 using the inserter tool 180. Once properly placed, the first body portion 714 may be rotated to its second position, so as to allow the implant 710 to expand to the expanded second width $W_1$. As shown, the expanded second width $W_1$ should be equal to the width in which the posterior arch portion 26 is to be expanded. Therefore, the implant 710 can be said to expand the implant receiving space from a first width to a second expanded width.

In another embodiment and in reference to FIGS. 19A and 19B, the implant may include a deformable body that is locked in a compressed position with a locking pin. As shown, an implant 810 includes a deformable body 814 and a pair of engagement members 818 that extend from opposed ends of the body 814. As shown in FIGS. 19A and 19B the body 814 initially defines an oblong ring having a bore 822 that extends therethrough. The body 814 further includes a pair of protrusions 826 that extend up within the bore 822 such that a recess 830 is defined between the protrusions 826, and a third protrusion 834 that opposes the protrusions 826 such that third protrusion 834 extends into the recess 830 when the body 814 is in a compressed configuration or position as shown in FIG. 19A. Each of the protrusions 826 and 834 defines a bore 838 that are configured to be aligned. The body 814 further includes a locking pin 842 that is configured to engage the bores 838 when the body 814 is in the compressed configuration or position to thereby hold the implant in the first or compressed configuration or position.

The body 814 further defines first and second opposed bone contacting surfaces 843*a* and 843*b* that are configured to engage the first and second posterior arch surfaces. When the body 814 is expanded from the first width to the second width, the first and second bone contacting surfaces 843*a* and 843*b* urge against the first and second posterior arch surfaces to thereby expand or otherwise widen the implant receiving space 46.

The engagement members 818 may have a variety of configurations so long as they are capable of engaging the lamina to thereby hold the implant 810 in place. For example, the engagement members 818, in the illustrated embodiment, each define a keel that includes a fixation element receiving aperture 840 configured to receive a fixation element such as a bone screw. The screws will engage the lamina to thereby fasten the implant 810 to the lamina.

In operation, the implant 810 may be implanted into the implant receiving space 46 of the lamina while in a compressed position such that the implant 810 defines a first width $W_0$ as shown in FIG. 19A. Once inserted, screws may be inserted through the bores 840 of the engagement members 818 and into the lamina to thereby affix the implant 810 to the lamina. The locking pin 842 may then be removed to thereby allow the body 814 and thus the implant receiving space 46 to expand to an expanded position such that the implant 810 and the implant receiving space 46 each defines a second expanded width $W_1$ as shown in FIG. 19B. Therefore, the implant 810 can be said to expand the implant receiving space 46 from a first width to a second expanded width.

In another embodiment and in reference to FIG. 20, the implant may include stops to prevent the implant from falling into the spinal canal during insertion. As shown, an implant 880 includes a body 884 having stops 888 that extend up from a surface of the body 884. The stops 888 are configured to contact the posterior arch portion 26 to prevent further insertion and avoid over insertion of the implant.

In another embodiment and in reference to FIG. 21, the implant may be a paddle plate. As shown, an implant 910 includes a plate 914 and a threaded screw 918 extending from an end of the plate 914. The plate 914 is substantially flat and defines a plurality of fixation element receiving apertures 922. While the plate 914 is shown as being flat, it should be understood that the plate 914 may be pre-curved or bent to adapt to the lamina shape.

In operation, the screw 918 is threaded into the lamina such that the plate 914 extends across the face of the implant receiving space 46. Using additional instrumentation such as pliers, the lamina is expanded. While expanded, screws may be inserted through the apertures 922 of the plate 914 and into the lamina to thereby affix the implant 910 to the lamina.

In another embodiment and in reference to FIG. 22, the implant may be a paddle plate with a hinge. As shown, an implant 950 includes a body that defines a plate 954, and further includes a threaded screw 958 extending from an end of the plate 954. The plate 954 is initially substantially flat and defines a plurality of fixation element receiving apertures 962. As shown, the plate 954 further defines a plurality of hinges 976 that allow the plate to be bent to create a hinged portion 980. As shown, the hinged portion 980 is configured to rotate about one of the hinges 976.

In operation, the implant 950 is inserted into the opening to assess the best position to bend the plate 954. Once determined the implant is removed and the plate 954 is bent about one of the hinges 976 to better fit the anatomy. The implant may then be reinserted into the opening and the screw 958 may be threaded into the lamina such that the plate 954 extends across the face of the implant receiving space 46. Using an spreading device such as pliers, the lamina is expanded. While expanded, screws may be inserted through the apertures 962 of the plate 954 and into the lamina to thereby affix the implant 950 to the lamina.

Now referring to FIGS. 23A and 23B, the implant assembly can include other configurations for inserting the implant. As shown, an implant assembly 1000 can include an inserter tool 1004 and an implant 1008 coupled to the inserter tool 10004. The inserter tool 1004 includes an elongate shaft 1012 and a coupler 1016 at a distal end of the shaft 1012. The coupler 1016 includes an external thread 1020 that is configured to engage internal threads defined by the implant 1008. Therefore, the implant receiving space 46 can be widened with a spreading device and the inserter tool 1004 can implant the implant 1008 into the widened implant receiving space 46. Once implanted, the inserter tool 1004 can be decoupled from the implant 1008. It should be appreciated that the coupler 1016 can include other configurations to releasably couple the inserter tool 1004 to the implant 1008. For example, the coupler 1016 can be a clip. The inserter tool 1004 can also be coupled to an expandable implant such as those shown in for example, FIGS. 11A, 12A, and 13. In such cases the implant receiving space can be widened, before, during, or even after implantation of the implant into the implant receiving space.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. For example, any of the implants described can include mating members as shown in FIG. 5A or engagement members to thereby couple the implant to the lamina. It is understood, therefore, that this invention is not limited to the particular embodiments disclosed, but it is intended to cover modifications within the spirit and scope of the present disclosure.

What is claimed:

1. A minimally invasive posterior arch expansion system configured to expand a spinal canal, the system comprising:
   an access member that is configured to define a minimally invasive access path along an insertion direction to an implant receiving space that is defined by first and second opposed posterior arch surfaces of a posterior arch portion;
   a spreading device configured to extend through the minimally invasive access path of the access member along the insertion direction and engage the first and second opposed posterior arch surfaces to thereby widen the implant receiving space such that the first and second posterior arch surfaces move away from each other toward a widened position; and
   an implant that is sized and configured to be inserted through the access member along the insertion direction and received in the implant receiving space between the first and second opposed posterior arch surfaces, the implant defining a leading end surface, a trailing end surface spaced from the leading end surface along the insertion direction, first and second opposed side surfaces extending from the leading end surface to the trailing end surface, and opposed upper and lower surfaces extending from the first side surface to the second side surface and from the leading end surface to the trailing end surface, the first and second side surfaces configured to abut the first and second opposed posterior arch surfaces, respectively, and the implant including a single first mating member that projects out from the first side surface and a single second mating member that projects out from the second side surface, wherein (i) the first and second mating members are positioned substantially at a midline of the first and second side surfaces along the insertion direction, (ii) a cross-section of the implant between the first and second mating members defines a first dimension from the first side surface at the first mating member to the second side surface at the second mating member that is greater than a second dimension from the upper surface to the lower surface at the cross-section, (iii) the implant has a third dimension from the leading end surface to the trailing end surface that is greater than both the first and second dimensions, (iv) the first and second mating members are configured to mate with recesses formed in the first and second posterior arch surfaces when the implant is implanted into the widened implant receiving space so as to maintain the implant receiving space in the widened position after the spreading device is removed, and (v) the implant includes a leading end and a trailing end, and the first and second side surfaces taper toward each other along the insertion direction from the trailing end to the leading end.

2. The minimally invasive posterior arch expansion system of claim 1, further comprising an inserter tool that is configured to extend through the minimally invasive access path of the access member to thereby insert the implant into the widened implant receiving space.

3. The minimally invasive posterior arch expansion system of claim 2, wherein the inserter tool includes a housing, and an elongate pusher that extends distally from the housing, the elongate pusher is configured to engage the implant, and wherein the spreading device includes first and second arms that extend distally from the housing on opposite sides of the elongate pusher, each of the first and second arms having an angled portion that angles toward the angled portion of the other arm, and an engagement portion that is distal to the elongate pusher.

4. The minimally invasive posterior arch expansion system of claim 3, wherein the engagement portions of the first and second arms are configured to engage the implant receiving space, and the elongate pusher is configured to advance the implant toward the implant receiving space such that the implant urges at least one of the angled portions of the first and second arms to move away from the other of the angled portions of the first and second arms, thereby causing the engagement portion of the urged angled portion to bias at least one of the first and second posterior arch surfaces away from the other of the first and second posterior arch surfaces so that the implant receiving space is sized to receive the implant.

5. The minimally invasive posterior arch expansion system of claim 4, wherein each of the first and second arms defines a rail that extends along a portion of a length of the arm toward the engagement portion, and wherein the mating members are each configured to engage a respective rail such that the implant rides along the rails as the implant is being advanced by the elongate pusher.

6. The minimally invasive posterior arch expansion system of claim 5, wherein the mating members are domed protrusions, each domed protrusion having a curvature along a first plane and a curvature along a second plane, perpendicular to the first plane.

7. The minimally invasive posterior arch expansion system of claim 6, wherein each domed portion is hemispherical.

8. The minimally invasive posterior arch expansion system of claim 5, wherein the rails are slots.

9. The minimally invasive posterior arch expansion system of claim 4, wherein the engagement portions of the first and second arms are flat panels that abut each other prior to the elongate pusher advancing the implant.

10. The minimally invasive posterior arch expansion system of claim 4, wherein each engagement portion includes a stop that is configured to limit insertion of the engagement portions into the implant receiving space.

11. The minimally invasive posterior arch expansion system of claim 1, wherein the leading surface has a length that is less than that of the trailing end surface.

12. The minimally invasive posterior arch expansion system of claim 11, wherein the leading end surface has a height that is less than that of the trailing end surface.

13. The minimally invasive posterior arch expansion system of claim 12, wherein the upper surface is planar as it extends from the leading end surface to the trailing end surface.

14. The minimally invasive posterior arch expansion system of claim 13, wherein the lower surface tapers toward the upper surface as the lower surface extends toward the leading surface along the insertion direction.

15. The minimally invasive posterior arch expansion system of claim 1, wherein the access member is a cannula having an elongate body that defines a distal end and a proximal end, the cannula further having a passageway that extends through the body from the proximal end to the distal end, the passageway of the cannula defining the minimally invasive access path to the implant receiving space.

16. The minimally invasive posterior arch expansion system of claim 15, wherein the passageway of the cannula has a cross sectional dimension that is between about 10 mm and about 25 mm, a distal end of the elongate body is configured to be positioned proximate to a vertebra of the cervical spine.

17. The minimally invasive posterior arch expansion system of claim 15, wherein the passageway of the cannula has a cross sectional dimension that is between about 15 mm and about 50 mm, a distal end of the elongate body is configured to be positioned proximate to a vertebra of the lumbar spine.

18. The minimally invasive posterior arch expansion system of claim 1, further comprising a cutting tool system that is configured to extend through the minimally invasive access path, the cutting tool system configured to cut at least partially into the posterior arch portion.

19. The minimally invasive posterior arch expansion system of claim 18, wherein the cutting tool system includes a rotary tool.

20. The minimally invasive posterior arch expansion system of claim 1, wherein the leading end surface defines a length that is less than that of the trailing end surface such that the first and second side surfaces taper toward each other along the insertion direction between the trailing end surface and the leading end surface.

21. The minimally invasive posterior arch expansion system of claim 1, wherein at least one of the upper surface, the lower surface, the leading end surface, and the trailing end surface includes a planar surface.

22. The minimally invasive posterior arch expansion system of claim 1, wherein the first and second side surfaces taper toward each other along the insertion direction at the first and second mating members.

23. The minimally invasive posterior arch expansion system of claim 1, wherein the first side surface is a first tapered side surface, the second side surface is a second tapered side surface, and the first and second mating members are disposed on the first and second tapered side surfaces, respectively.

24. A minimally invasive posterior arch expansion system configured to insert an implant along an insertion direction into an implant receiving space defined by first and second posterior arch surfaces, the system comprising:
an elongate pusher that defines a proximal end and a distal end opposite the proximal end, the elongate pusher having a biasing member at the distal end;
first and second arms that are disposed on opposite sides of the elongate pusher, each of the first and second arms having an angled portion that angles toward the angled portion of the other arm along a direction from the proximal end toward the distal end, each of the first and second arms further including an engagement portion that is disposed distally of the biasing member, wherein the engagement portions of the first and second arms are configured to face the first and second posterior arch surfaces, respectively;
an implant sized and configured to be received in the implant receiving space between the first and second posterior arch surfaces, the implant defining a leading end surface, a trailing end surface spaced from the leading end surface along the insertion direction, first and second opposed side surfaces extending from the leading end surface to the trailing end surface, and opposed upper and lower surfaces extending from the first side surface to the second side surface and from the leading end surface to the trailing end surface, the leading end surface defining a length that is less than that of the trailing end surface such that the first and second side surfaces taper toward each other along the insertion direction between the trailing end surface and the leading end surface, wherein the implant includes a single first domed protrusion that projects out from the first side surface and a single second domed protrusion that projects out from the second side surface such that the first and second domed protrusions are positioned substantially at a midline of the first and seconds side surfaces along the insertion direction and a cross-section of the implant between the first and second mating members defines a first dimension from the first side surface at the first mating member to the second side surface at the second mating member that is greater than a second dimension from the upper surface to the lower surface at the cross-section, the first and second domed protrusions being configured to mate with the first and second arms respectively such that the implant is configured to ride along the first and second arms at a location distal to the biasing member, being sized to mate with respective recesses formed in the first and second posterior arch surfaces such that the first and second domed protrusions lock the implant within the implant receiving space when the implant is received by the implant receiving space, and each having a curvature along a first plane and a curvature along a second plane, perpendicular to the first plane;
wherein the biasing member is configured to advance the implant toward the implant receiving space such that the implant urges at least one of the angled portions of the first and second arms to move away from the other of the angled portions of the first and second arms as the implant rides along the first and second arms, thereby causing the engagement portion of the urged at least one arm to bias at least one of the first and second posterior arch surfaces away from the other of the first and second posterior arch surfaces so that the recesses are positioned to receive the domed protrusions.

25. The minimally invasive posterior arch expansion system of claim 24, wherein the leading end surface has a height that is less than that of the trailing end surface.

26. The minimally invasive posterior arch expansion system of claim 25, wherein the upper surface is planar as it extends from the leading end surface to the trailing end surface.

27. The minimally invasive posterior arch expansion system of claim 26, wherein the lower surface tapers toward the upper surface as the lower surface extends toward the leading surface along the insertion direction.

28. The minimally invasive posterior arch expansion system of claim 24, wherein each of the first and second arms defines a rail that extends along a portion of a length of the arm toward the engagement portion, and wherein the domed protrusions are each configured to engage a respective rail such that the implant rides along the rails as the implant is being advanced by the elongate pusher.

29. The minimally invasive posterior arch expansion system of claim 28, wherein the rails are slots.

30. The minimally invasive posterior arch expansion system of claim 24, wherein the implant has a third dimension from the leading end surface to the trailing end surface that is greater than the second dimension.

31. The minimally invasive posterior arch expansion system of claim 30, wherein the third dimension is greater than the first dimension.

32. The minimally invasive posterior arch expansion system of claim 24, wherein the engagement portions of the first and second arms are flat panels that abut each other prior to the elongate pusher advancing the implant.

33. The minimally invasive posterior arch expansion system of claim 24, wherein each engagement portion includes a stop that is configured to limit insertion of the engagement portions into the implant receiving space.

34. The minimally invasive posterior arch expansion system of claim 24, wherein each domed portion is hemispherical.

35. The minimally invasive posterior arch expansion system of claim 24, wherein at least one of the upper surface, the lower surface, the leading end surface, and the trailing end surface includes a planar surface.

36. The minimally invasive posterior arch expansion system of claim 24, wherein the first and second side surfaces taper toward each other along the insertion direction at the first and second domed protrusions.

* * * * *